(12) United States Patent
Zhang

(10) Patent No.: US 8,815,507 B2
(45) Date of Patent: Aug. 26, 2014

(54) METHOD AND MATERIALS FOR THE COOPERATIVE HYBRIDIZATION OF OLIGONUCLEOTIDES

(75) Inventor: David Zhang, Overland Park, KS (US)

(73) Assignee: California Institute of Technology, Pasadena, CA (US)

(*) Notice: Subject to any disclaimer, the term of this patent is extended or adjusted under 35 U.S.C. 154(b) by 155 days.

(21) Appl. No.: 13/051,602

(22) Filed: Mar. 18, 2011

(65) Prior Publication Data

US 2011/0306758 A1  Dec. 15, 2011

Related U.S. Application Data

(60) Provisional application No. 61/315,279, filed on Mar. 18, 2010.

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |
| C12N 15/11 | (2006.01) | |
| C07H 21/00 | (2006.01) | |

(52) U.S. Cl.
CPC .............. *C07H 21/00* (2013.01); *C12N 15/111* (2013.01); *C12Q 1/6823* (2013.01); *C12Q 1/6832* (2013.01); *C12N 2320/50* (2013.01)
USPC ......... 435/6.1; 435/6.11; 435/91.1; 536/23.1; 536/24.3; 536/24.33

(58) Field of Classification Search
USPC .................... 435/6.1, 6.11, 91.1; 436/94, 501; 536/23.1, 24.3, 24.33
See application file for complete search history.

(56) References Cited

U.S. PATENT DOCUMENTS

2007/0264265 A1   11/2007   Goldenberg et al.

OTHER PUBLICATIONS

Aldaye et al., "Assembling Materials with DNA as the Guide", Science, Sep. 26, 2008, vol. 321, pp. 1795-1799.
Andersen et al., "Self-Assembly of a Nanoscale DNA Box With a Controllable Lid", Nature, May 7, 2009, vol. 459, pp. 73-77.
Bartel, "MicroRNAs: Target Recognition and Regulatory Functions", Cell, Jan. 23, 2009, vol. 136, pp. 215-233.
Bath et al., "DNA Nanomachines", Nature Nanotechnology, May 2007, vol. 2, pp. 275-284.
Bunka et al., "Aptamers Come of Age—At Last", Nature, Aug. 2006, vol. 4, pp. 588-596.
Carlson, "The Changing Economics of DNA Synthesis", Nature Biotechnology, Dec. 2009, vol. 27, No. 12, pp. 1091-1094.
Ding et al., "Operation of a DNA Robot Arm Inserted into a 2D DNA Crystalline Substrate", Science, Dec. 8, 2006, vol. 314, pp. 1583-1585.
Dirks et al., "Triggered Amplification by Hybridization Chain Reaction", PNAS, Oct. 26, 2004, vol. 101, No. 43, pp. 15275-15278.
Douglas et al., "Self-Assembly of DNA Into Nanoscale Three-Dimensional Shapes", Nature, May 21, 2009, vol. 459, pp. 414-418, 1154.

(Continued)

*Primary Examiner* — Frank Lu
(74) *Attorney, Agent, or Firm* — KPPB LLP

(57) ABSTRACT

A two-stranded intermediary complex and cooperative hybridization method are provided. The complex has been designed so that target oligonucleotides of independent sequence can cooperatively and simultaneously hybridize to it. The cooperative hybridization mechanism is robust and modular, smoothly integrating with other dynamic DNA components to form cascaded reaction networks that can perform a variety of functions.

41 Claims, 12 Drawing Sheets

(56) References Cited

OTHER PUBLICATIONS

Frezza et al., "Modular Multi-Level Circuits from Immobilized DNA-Based Logic Gates", J. Am. Chem. Soc, 2007, vol. 129, pp. 14875-14879.

Gao et al., "Secondary Structure Effects on DNA Hybridization Kinetics: A Solution Versus Surface Comparison", Nucleic Acids Research, Jul. 5, 2006, vol. 34, No. 11, pp. 3370-3377.

Gartner et al., "DNA-Templated Organic Synthesis and Selection of a Library of Macrocycles", Science, Sep. 10, 2004, vol. 305, pp. 1601-1605.

Green et al., "Coordinated Chemomechanical Cycles: A Mechanism for Autonomous Molecular Motion", Physical Review Letters, Dec. 3, 2008, vol. 101, No. 238101, pp. 1-4.

Gu et al., "A Proximity-Based Programmable DNA Nanoscale Assembly Line", Nature, May 13, 2010, vol. 465, pp. 202-206.

Hamilton et al., "A Species of Small Antisense RNA in Post-transcriptional Gene Silencing in Plants", Science, Oct. 29, 1999, vol. 286, pp. 950-952.

Isaacs et al., "Engineered Riboregulators Enable Post-Transcriptional Control of Gene Expression", Nature Biotechnology, Jul. 2004, vol. 22, No. 7, pp. 841-847.

Joyce, "Directed Evolution of Nucleic Acid Enzymes", Annu. Rev. Biochem, 2004, vol. 73, pp. 791-836.

Krueger et al., "Redesigning the Architecture of the Base Pair: Toward Biochemical and Biological Function of New Genetic Sets", Chemistry & Biology, Mar. 27, 2009, vol. 16, pp. 242-248.

Lederman et al., "Deoxyribozyme-Based Three-Input Logic Gates and Construction of a Molecular Full Adder", Biochemistry, 2006, vol. 45, No. 4, pp. 1194-1199.

Levy et al., "Exponential Growth by Cross-Catalytic Cleavage of Deoxyribozymogens", PNAS, May 27, 2003, vol. 100, No. 11, pp. 6416-6421.

Lu et al., "Functional DNA Nanotechnology: Emerging Applications of DNAzymes and Aptamers", Current Opinion in Biotechnology, 2006, vol. 17, pp. 580-588.

Lu et al., "MicroRNA Expression Profiles Classify Human Cancers", Nature, Jun. 9, 2005, vol. 435, pp. 834-838.

Lund et al., "Molecular Robots Guided by Prescriptive Landscapes", Nature, May 13, 2010, vol. 465, pp. 206-210.

Mao et al., "A Nanomechanical Device Based on the B-Z Transition of DNA", Nature, Jan. 14, 1999, vol. 397, pp. 144-146.

Marras et al., "Efficiencies of Fluorescence Resonance Energy Transfer and Contact-Mediated Quenching in Oligonucleotide Probes", Nucleic Acids Research, 2002, vol. 30, No. 21, pp. 1-8.

Maune et al., "Self-Assembly of Carbon Nanotubes Into Two-Dimensional Geometries Using DNA Origami Templates", Nature Nanotechnology, Jan. 2010, vol. 5, pp. 61-66.

Omabegho et al., "A Bipedal DNA Brownian Motor with Coordinated Legs", Science, Apr. 3, 2009, vol. 324, pp. 67-71.

Owczarzy et al., "Predicting Stability of DNA Duplexes in Solutions Containing Magnesium and Monovalent Cations", Biochemistry, 2008, vol. 47, pp. 5336-5353.

Pyshnyi et al., "The Influence of Nearest Neighbours on the Efficiency of Coaxial Stacking at Contiguous Stacking Hybridization of Oligodeoxyribonucleotides", Nucleosides, Nucleotides & Nucleic Acids, 2004, vol. 23, No. 6 & 7, pp. 1057-1064.

Rinker et al., "Self-Assembled DNA Nanostructures for Distance-Dependent Multivalent Ligand—Protein Binding", Nature Nanotechnology, Jul. 2008, vol. 3, pp. 418-422.

Rosi et al., "Nanostructures in Biodiagnostics", Chemical Reviews, 2005, vol. 105, No. 4, pp. 1547-1562.

Rothemund, "Folding DNA to Create Nanoscale Shapes and Patterns", Nature, Mar. 16, 2006, vol. 440, pp. 297-302.

Rothemund et al., "Algorithmic Self-Assembly of DNA Sierpinski Triangles", PLOS Biology, Dec. 2004, vol. 2, No. 12, pp. 2041-2053.

Santalucia et al., "The Thermodynamics of DNA Structural Motifs", Annual Review of Biophysics and Biomolecular Structure 2004, vol. 33, pp. 415-440.

Seelig et al., "Catalyzed Relaxation of a Metastable DNA Fuel", J. Am. Chemical Society, 2006, vol. 128, pp. 12211-12220.

Seelig et al., "Enzyme-Free Nucleic Acid Logic Circuits", Science, Dec. 8, 2006, vol. 314, pp. 1585-1588.

Seferos et al., "Nano-Flares: Probes for Transfection and mRNA Detection in Living Cells", J. American Chemical Society, 2007, vol. 129, pp. 15477-15479.

Shih et al., "Knitting Complex Weaves With DNA Origami", Current Opinion in Structural Biology, 2010, vol. 20, pp. 276-282.

Soloveichik et al., "DNA as a Universal Substrate for Chemical Kinetics", PNAS, Mar. 23, 2010, vol. 107, No. 12, pp. 5393-5398.

Stojanovic et al., "A Deoxyribozyme-Based Molecular Automaton", Nature Biotechnology, Sep. 2003, vol. 21, No. 9, pp. 1069-1074.

Tyagi et al., "Molecular Beacons: Probes that Fluoresce Upon Hybridization", Nature Biotechnology, Mar. 1996, vol. 14, pp. 303-308.

Venkataraman et al., "An Autonomous Polymerization Motor Powered by DNA Hybridization", Nature Nanotechnology, Aug. 2007, vol. 2, pp. 490-494.

Venkataraman et al., "Selective Cell Death Mediated by Small Conditional RNAs", PNAS, Sep. 28, 2010, vol. 107, No. 39, pp. 16777-16782.

Willner et al., "DNAzymes for Sensing, Nanobiotechnology and Logic Gate Applications", Chemical Society Reviews, 2008, vol. 37, pp. 1153-1165.

Win et al., "Higher-Order Cellular Information Processing with Synthetic RNA Devices", Science, Oct. 17, 2008, vol. 322, pp. 456-460.

Winfree et al., "Design and Self-Assembly of Two-Dimensional DNA Crystals", Nature, Aug. 6, 1998, vol. 394, pp. 539-544.

Xie et al., "Logic Integration of mRNA Signals by an RNAi-Based Molecular Computer", Nucleic Acids Research, 2010, vol. 38, No. 8, pp. 2692-2701.

Yan et al., "A Robust DNA Mechanical Device Controlled by Hybridization Topology", Nature, Jan. 3, 2002, vol. 415, pp. 62-65.

Yin et al., Programming biomolecular self-assembly pathways, Nature, Jan. 17, 2008, vol. 451, pp. 318-322.

Yurke et al., "A DNA-Fuelled Molecular Machine Made of DNA", Nature, Aug. 10, 2000, vol. 406, pp. 605-608.

Zamore et al., "RNAi: Double-Stranded RNA Directs the ATP-Dependent Cleavage of mRNA at 21 to 23 Nucleotide Intervals", Cell, Mar. 31, 2000, vol. 101, pp. 25-33.

Zhang et al., "Control of DNA Strand Displacement Kinetics Using Toehold Exchange", J. Am. Chem. Soc., 2009, vol. 131, pp. 17303-17314.

Zhang et al., "Dynamic Allosteric Control of Noncovalent DNA Catalysis Reactions", J. Am. Chem. Soc., 2008, vol. 130, pp. 13921-13926.

Zhang et al., "Dynamic DNA Nanotechnology Using Strand-Displacement Reactions", Nature Chemistry, Feb. 2011, vol. 3, pp. 103-113.

Zhang et al., "Engineering Entropy-Driven Reactions and Networks Catalyzed by DNA", Science, Nov. 16, 2007, vol. 318, pp. 1121-1125, 1 pg erratum.

Zheng et al., "From Molecular to Macroscopic Via the Rational Design of a Self-Assembled 3D DNA Crystal", Nature, Sep. 3, 2009, vol. 461, pp. 74-77.

O'Keefe et al., "Potent Anti-Influenza Activity of Cyanovirin-N and Interactions with Viral Hemagglutinin", Antimicrobial Agents and Chemotherapy, Aug. 2003, vol. 47, No. 8, pp. 2518-2525.

Ong et al., "A Global Perspective on Avian Influenza", Ann Acad Med Singapore, Jun. 2008, vol. 37, No. 6, pp. 477-481.

Presta, "Molecular engineering and design of therapeutic antibodies", Immunology, 2008, vol. 20, pp. 460-470.

Presta, "Selection, design, and engineering of therapeutic antibodies", J Allergy Clin Immunol, Oct. 2005, vol. 116, pp. 731-736.

Proenca-Modena et al., "H5N1 Avian Influenza Virus: An Overview", The Brazilian Journal of Infectious Diseases, 2007, vol. 11, No. 1, pp. 125-133.

Raghavan et al., "Fc Receptors and their Interactions with Immunoglobulins", Annu. Rev. Cell Dev. Biol., 1996, vol. 12, pp. 181-220.

(56) References Cited

OTHER PUBLICATIONS

Reid et al., "The origin of the 1918 pandemic influenza virus: a continuing enigma", Journal of General Virology, 2003, vol. 84, pp. 2285-2292.
Reitter et al., "A role for carbohydrates in immune evasion in AIDS", Nature Medicine, Jun. 1998, vol. 4, No. 6, pp. 679-684.
Saphire et al., "Crystal Structure of a Neutralizing Human IgG Against HIV-1: A Template for Vaccine Design", Science, Aug. 10, 2001, vol. 293, pp. 1155-1159.
Sattentau et al., "Conformational Changes Induced in the Human Immunodeficiency Virus Envelope Glycoprotein by Soluble CD4 Binding", J. Exp. Med., Aug. 1991, vol. 174, pp. 407-415.
Shafer et al., "HIV-1 Drug Resistance Mutations: an Updated Framework for the Second Decade of HAART", AIDS, Rev. 2008, vol. 10, pp. 67-84.
Shapiro et al., "Expression of Sonic hedgehog-Fc fusion protein in *Pichia pastoris*. Identification and control of post-translational, chemical, and proteolytic modifications", Protein Expression and Purification, 2003, vol. 29, pp. 272-283.
Shenoy et al., "Multisite and Multivalent Binding between Cyanovirin-N and Branched Oligomannosides: Calorimetric and NMR Characterization", Chemistry & Biology, Oct. 2002, vol. 9, pp. 1109-1118.
Shenoy et al., "Selective Interactions of the Human Immunodeficiency Virus-Inactivating Protein Cyanovirin-N with High-Mannose Oligosaccharides on gp120 and Other Glycoproteins", The Journal of Pharmacology and Experimental Therapeutics, 2001, vol. 297, No. 2, pp. 704-710.
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, Mar. 2, 2001, vol. 276, No. 9, pp. 6591-6604.
Shields et al., "Lack of Fucose on Human IgG1 N-Linked Oligosaccharide Improves Binding to Human FcγRIII and Antibody-dependent Cellular Toxicity", The Journal of Biological Chemistry, Jul. 26, 2002, vol. 277, No. 30, pp. 26733-26740.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", The Journal of Biological Chemistry, Jan. 31, 2003, vol. 278, No. 5, pp. 3466-3473.
Uger et al., "Creating CTL targets with epitope-linked beta2-microglobulin constructs, J. Immunol. 160:1598-1605"1998.
Ahmad et al., "Evidence for a Correlation Between Antibody-Dependent Cellular Cytotoxicity-Mediating Anti-HIV-1 Antibodies and Prognostic Predictors of HIV Infection", Journal of Clinical Immunology, 2001, vol. 21, No. 3, pp. 227-233.
Ahmad et al., "Surface Expression of the HIV-1 Envelope Proteins in env Gene-Transfected CD4-Positive Human T Cell Clones: Characterization and Killing by an Antibody-Dependent Cellular Cytotoxic Mechanism", Journal of Acquired Immune Deficiency Syndromes, 1994, pp. 789-798.
Ashkenazi et al., "Immunoadhesins", Intern. Rev. Immunol., 1993, vol. 10, pp. 219-227.
Baenziger et al., "Disseminated and sustained HIV infection in CD34+ cord blood cell-transplanted Rag2-/-γc -/- mice", PNAS, Oct. 24, 2006, vol. 103, No. 43, pp. 15951-15956.
Baldridge et al., "Mechanisms of Antibody-Mediated Protection against Lymphocytic Choriomeningitis Virus Infection: Mother-to-Baby Transfer of Humoral Protection", Journal of Virology, Jul. 1992, pp. 4252-4257.
Balzarini, "Targeting the glycans of glycoproteins: a novel paradigm for antiviral therapy", Microbiology, Aug. 2007, vol. 5, pp. 583-597.
Balzarini et al., "Carbohydrate-binding Agents Cause Deletions of Highly Conserved Glycosylation Sites in HIV GP120", The Journal of Biological Chemistry, Dec. 9, 2005, vol. 280, No. 49, pp. 41005-41014.
Balzarini et al., "Marked Depletion of Glycosylation Sites in HIV-1 gp120 under Selection Pressure by the Mannose-Specific Plant Lectins of Hippeastrum Hybrid and *Galanthus nivalis*", Molecular Pharmacology, 2005, vol. 67, No. 5, pp. 1556-1565.
Balzarini et al., "Mutational Pathways, Resistance Profile, and Side Effects of Cyanovirin Relative to Human Immunodeficiency Virus Type 1 Strains with N-Glycan Deletions in Their gp120 Envelopes", Journal of Virology, Sep. 2006, vol. 80, No. 17, pp. 8411-8421.
Barrientos et al., "Cyanovirin-N binds to the viral surface glycoprotein, GP1,2 and inhibits infectivity of Ebola virus", Antiviral Research, 2003, vol. 58, pp. 47-56.
Barrientos et al., "Design and Initial Characterization of a Circular Permuted Variant of the Potent HIV-Inactivating Protein Cyanovirin-N", Proteins: Structure, Function, and Genetics, 2002, vol. 46, pp. 153-160.
Barrientos et al., "Flipping the Switch from Monomeric to Dimeric CV-N Has Little Effect on Antiviral Activity", Structure, Oct. 2004, vol. 12, pp. 1799-1807.
Barrientos et al., "The Domain-Swapped Dimer of Cyanovirin-N Is in a Metastable Folded State: Reconciliation of X-Ray and NMR Structures", Structure, May 2002, vol. 10, pp. 673-686.
Barrientos et al., "The Highly Specific Carbohydrate-Binding Protein Cyanovirin-N: Structure, Anti-HIV/Ebola Activity and Possibilities for Therapy", Mini-Reviews in Medicinal Chemistry, 2005, vol. 5, pp. 21-31.
Becktel et al., "Protein Stability Curves", Biopolymers, 1987, vol. 26, pp. 1859-1877.
Bewley, "Solution Structure of a Cyanovirin-N:Man 1-2Man Complex: Structural Basis for High Affinity Carbohydrate-Mediated Binding to gp120", Structure, Oct. 2001, vol. 9, pp. 931-940.
Bewley et al., "Solution structure of cyanovirin-N, a potent HIV-inactivating protein", Nature Structural Biology, Jul. 1998, vol. 5, No. 7, pp. 571-578.
Bewley et al., "The Potent Anti-HIV Protein Cyanovirin-N Contains Two Novel Carbohydrate Binding Sites That Selectively Bind to Man8, DID3 and Man9 with Nanomolar Affinity: Implications for Binding to the HIV Envelope Protein gp120", J. Am. Chem. Soc., 2001, vol. 123, pp. 3892-3902.
Bl et al., "Structural features of galectin-9 and galectin-1 that determine distinct T-cell death pathways", J. Biol. Chem., May 2008, vol. 283, No. 18, pp. 12248-12258.
Binley et al., "Comprehensive Cross-Clade Neutralization Analysis of a Panel of Anti-Human Immunodeficiency Virus Type 1 Monoclonal Antibodies", Journal of Virology, Dec. 2004, vol. 78, No. 23, pp. 13232-13252.
Bitonti et al., "Pulmonary delivery of an erythropoietin Fc fusion protein in non-human primates through an immunoglobulin transport pathway", PNAS, Jun. 29, 2004, vol. 101, No. 26, pp. 9763-9768.
Bolmstedt et al., "Cyanovirin-N Defines a New Class of Antiviral Agent Targeting N-Linked, High-Mannose Glycans in an Oligosaccharide-Specific Manner", Molecular Pharmacology, 2001, vol. 59, No. 5, pp. 949-954.
Boraston et al., "Carbohydrate-binding modules: fine-tuning polysaccharide recognition, Biochem. J. 382:"2004, 769-781.
Botos et al., "Cyanovirin-N: a sugar-binding antiviral protein with a new twist", CMLS, Cell. Mol. Life Sci., 2003, vol. 60, pp. 277-287.
Botos et al., "Domain-swapped structure of a mutant of cyanovirin-N", Biochemical and Biophysical Research Communications, 2002, vol. 294, pp. 184-190.
Botos et al., "Structures of the Complexes of a Potent Anti-HIV Protein Cyanovirin-N And High Mannose Oligosaccharides", The Journal of Biological Chemistry, Sep. 13, 2002, vol. 277, No. 37, pp. 34336-34342.
Boyd et al., "Discovery of Cyanovirin-N, a Novel Human Immunodeficiency Virus-Inactivating Protein That Binds Viral Surface Envelope Glycoprotein gp120: Potential Applications to Microbicide Development", Antimicrobial Agents and Chemotherapy, Jul. 1997, vol. 41, No. 7, pp. 1521-1530.
Bringans et al., "Development of a fluorescent microplate assay for determining cyanovirin-N levels in plasma", Anal Bioanal Chem, 2004, vol. 380, pp. 269-274.
Brunger, "Version 1.2 of the Crystallography and NMR system", Nature Protocols, 2007, vol. 2, No. 11, pp. 2728-2733.

(56) References Cited

OTHER PUBLICATIONS

Brunger et al., "Crystallography & NMR System: A New Software Suite for Macromolecular Structure Determination", Acta Cryst., 1998, vol. D54, pp. 905-921.
Burton et al., "Antibody vs. HIV in a clash of evolutionary titans", PNAS, Oct. 18, 2005, vol. 102, No. 42, pp. 14943-14948.
Burton et al., "Efficient Neutralization of Primary Isolates of HIV-1 by a Recombinant Human Monoclonal Antibody", Science, New Series, Nov. 11, 1994, vol. 266, No. 5187, pp. 1024-1027.
Burton et al., "HIV vaccine design and the neutralizing antibody problem", Nature Immunology, Mar. 2004, vol. 5, No. 3, pp. 233-236.
Byrn et al., "Biological properties of a CD4 immunoadhesin", Nature, Apr. 12, 1990, vol. 344, pp. 667-670.
Calarese et al., "Antibody Domain Exchange is an Immunological Solution to Carbohydrate Cluster Recognition", Science, Jun. 27, 2003, vol. 300, pp. 2065-2071.
Capon et al., "Designing CD4 immunoadhesins for AIDS therapy", Nature, Feb. 9, 1989, vol. 337, pp. 525-531.
Cardoso et al., "Broadly Neutralizing Anti-HIV Antibody 4E10 Recognizes a Helical Conformation of a Highly Conserved Fusion-Associated Motif in gp41", Immunity, Feb. 2005, vol. 22, pp. 163-173.
Charnow et al., "Immunoadhesins: principles and applications", Tibtech, Feb. 1996, vol. 14, pp. 52-60.
Cheung et al., "Distribution of Amantadine-Resistant H5N1 Avian Influenza Variants in Asia", JID, Jun. 15, 2006, vol. 193, pp. 1626-1629.
Collaborative Computational, Project, No. 4 , "The CCP4 Suite: Programs for Protein Crystallography", Acta Cryst., 1994, vol. D50, pp. 760-763.
Colleluori et al., "Expression, purification, and characterization of recombinant cyanovirin-N For vaginal anti-HIV microbicide development", Protein Expression and Purification, 2005, vol. 39, pp. 229-236.
Dacheux et al., "Evolutionary Dynamics of the Glycan Shield of the Human Immunodeficiency Virus Envelope during Natural Infection and Implications for Exposure of the 2G12 Epitope", Journal of Virology, Nov. 2004, vol. 78, No. 22, pp. 12625-12637.
Daeron, "Fc Receptor Biology", Annu. Rev. Immunol., 1997, vol. 15, pp. 203-234.
De Jong et al., "Oseltamivir Resistance during Treatment of Influenza a (H5N1) Infection", N Engl J Med, Dec. 22, 2005, vol. 353, No. 25, pp. 2667-2672.
Dey et al., "Multiple Antiviral Activities of Cyanovirin-N: Blocking of Human Immunodeficiency Virus Type 1 gp120 Interaction with CD4 and Coreceptor and Inhibition of Diverse Enveloped Viruses", Journal of Virology, May 2000, vol. 74, No. 10, pp. 4562-4569.
Dumont et al., "Delivery of an Erythropoietin-Fc Fusion Protein by Inhalation in Humans through an Immunoglobulin Transport Pathway", Journal of Aerosol Medicine, 2005, vol. 18, No. 3, pp. 294-303.
Dwyer et al., "Expression and Characterization of a DNase I-Fc Fusion Enzyme", The Journal of Biological Chemistry, Apr. 2, 1999, vol. 274, No. 14, pp. 9738-9743.
Emmert, "Treatment of Common Cutaneous Herpes Simplex Virus Infections", The American Academy of Family Physicians, Mar. 15, 2000, pp. 1-9.
Emsley et al., "Coot: model-building tools for molecular graphics", Acta Cryst., 2004, vol. D60, pp. 2126-2132.
Endsley et al., "Combining Drug and Immune Therapy: A Potential Solution to Drug Resistance and Challenges of HIV Vaccines?", Current HIV Research, 2008, vol. 6, pp. 401-410.
Enserink, "New Vaccine and Treatment Excite Ebola Researchers", Science, Nov. 14, 2003, vol. 302, pp. 1141-1142.
Esser et al., "Cyanovirin-N Binds to gp120 to Interfere with CD4-Dependent Human Immunodeficiency Virus Type 1 Virion Binding, Fusion, and Infectivity but Does Not Affect the CD4 Binding Site on gp120 or Soluble CD4-Induced Conformational Changes in gp120", Journal of Virology, May 1999, vol. 73, No.5, pp. 4360-4371.
Fenouillet et al., "Role of N-Linked Glycans of Envelope Glycoproteins in Infectivity of Human Immunodeficiency Virus Type 1", Journal of Virology, Jun. 1990, vol. 64, No. 6, pp. 2841-2848.
Florese et al., "Evaluation of Passively Transferred, Nonneutralizing Antibody-Dependent Cellular Cytotoxicity-Mediating IgG in Protection of Neonatal Rhesus Macaques against Oral SIVmac251 Challenge", The Journal of Immunology, 2006, vol. 177, pp. 4028-4036.
Fromme et al., "A Monovalent Mutant of Cyanovirin-N Provides Insight into the Role of Multiple Interactions with gp120 for Antiviral Activity", Biochemistry, 2007, vol. 46, pp. 9199-9207.
Fromme et al., "Conformational gating of dimannose binding to the antiviral protein cyanovirin revealed from the crystal structure at 1.35 A resolution", Protein Science, 2008, vol. 17, pp. 939-944.
Gessner et al., "The IgG Fc receptor family", Ann Hematol, 1998, vol. 76, pp. 231-248.
Gomez-Roman et al., "Vaccine-Elicited Antibodies Mediate Antibody-Dependent Cellular Cytotoxicity Correlated with Significantly Reduced Acute Viremia in Rhesus Macaques Challenged with SIVmac251 1", The Journal of Immunology, 2005, vol. 174, pp. 2185-2189.
Gupta et al., "Targeted lysis of HIV-infected cells by natural killer cells armed and triggered by a recombinant immunoglobulin fusion protein: implications for immunotherapy", Virology, 2005, vol. 332, pp. 491-497.
Gurbaxani et al., "Development of new models for the analysis of Fc-FcRn interactions", Molecular Immunology, 2006, vol. 43, pp. 1379-1389.
He et al., "Amantadine-resistance among H5N1 avian influenza viruses isolated in Northern China", Antiviral Research, 2008, vol. 77, pp. 72-76.
Hedestam et al., "The challenges of eliciting neutralizing antibodies to HIV-1 and to influenza virus", Microbiology, Feb. 2008, vol. 6, pp. 143-155.
Helle et al., "Cyanovirin-N Inhibits Hepatitis C Virus Entry by Binding to Envelope Protein Glycans", The Journal of Biological Chemistry, Sep. 1, 2006, vol. 281, No. 35, pp. 25177-25183.
Hessell et al., "Fc receptor but not complement binding is important in antibody protection against HIV", Nature, Sep. 6, 2007, vol. 449, pp. 101-105.
Hinton et al., "An Engineered Human IgG1 Antibody with Longer Serum Half-Life", The Journal of Immunology, 2006, vol. 176, pp. 346-356.
Hinton et al., "Engineered Human IgG Antibodies with Longer Serum Half-lives in Primates", The Journal of Biological Chemistry, Feb. 20, 2004, vol. 279, No. 8, pp. 6213-6216.
Holl et al., "Efficient inhibition of HIV-1 replication in human immature monocyte-derived dendritic cells by purified anti-HIV-1 IgG without induction of maturation", Blood, Jun. 1, 2006, vol. 107, No. 11, pp. 4466-4474.
Holl et al., "Nonneutralizing Antibodies Are Able to Inhibit Human Immunodeficiency Virus Type 1 Replication in Macrophages and Immature Dendritic Cells", Journal of Virology, Jun. 2006, vol. 80, No. 12, pp. 6177-6181.
Hu et al., "High-mannose-specific deglycosylation of HIV-1 gp120 induced by resistance to cyanovirin-N and the impact on antibody neutralization", Virology, 2007, vol. 368, pp. 145-154.
Huber et al., "Fc Receptor-Mediated Phagocytosis Makes a Significant Contribution to Clearance of Influenza Virus Infections", The Journal of Immunology, 2001, vol. 166, pp. 7381-7388.
Huber et al., "Humoral immunity to HIV-1: neutralization and beyond", J Intern Med, 2007, vol. 262, pp. 5-25.
Idusogie et al., "Engineered Antibodies with Increased Activity to Recruit Complement", The Journal of Immunology, 2001, vol. 166, pp. 2571-2575.
Imperiali et al., "Effect of N-linked glycosylation on glycopeptide and glycoprotein structure", Chemical Biology, 1999, vol. 3, pp. 643-649.
Jazayeri et al., "Fc-Based Cytokines", Biodrugs, 2008, vol. 22, No. 1, pp. 11-26.
Jefferis et al., "IgG-Fc-mediated effector functions: molecular definition of interaction sites for effector ligands and the role of glycosylation", Immunological Reviews, 1998, vol. 163, pp. 59-76.

(56) References Cited

OTHER PUBLICATIONS

Ji et al., "Mannose binding lectin (MBL) and HIV", Mol. Immunol., 2005, vol. 42, pp. 145-152.
Kang et al., "Modified HIV envelope proteins with enhanced binding to neutralizing monoclonal antibodies", Virology, 2005, vol. 331, pp. 20-32.
Keeffee et al., "Designed oligomers of cyanovirin-N show enhanced HIV neutralization", PNAS, Aug. 23, 2011, vol. 108, No. 34, pp. 14079-14084.
Kelley et al., "Engineering an Obligate Domain-Swapped Dimer of Cyanovirin-N with Enhanced Anti-HIV Activity", J. Am. Chem. Soc., 2002, vol. 124, pp. 3210-3211.
Krug, "The potential use of influenza virus as an agent for bioterrorism", Antiviral Research, 2003, vol. 57, pp. 147-150.
Kwong et al., "Structure of an HIV gp120 envelope glycoprotein in complex with the CD4 receptor and a neutralizing human antibody", Nature, Jun. 18, 1998, vol. 393, pp. 648-659.
Labrijn et al., "Access of Antibody Molecules to the Conserved Coreceptor Binding Site on Glycoprotein gp120 is Sterically Restricted on Primary Human Immunodeficiency Virus Type 1", Journal of Virology, Oct. 2003, vol. 77, No. 19, pp. 10557-10565.
Langner et al., "Antiviral effects of different CD4-immunoglobulin constructs against HIV-1 and SIV: immunological characterization, pharmacokinetic data and in vivo experiments", Arch Virol, 1993, vol. 130, pp. 157-170.
Lazar et al., "Engineered antibody Fc variants with enhanced effector function", PNAS, Mar. 14, 2006, vol. 103, No. 11, pp. 4005-4010.
Le et al., "Isolation of drug-resistant H5N1 virus", Nature, Oct. 20, 2005, vol. 437, 1 pg.
Legrand et al., "Experimental Models to Study Development and Function of the Human Immune System in Vivo", The Journal of Immunology, 2006, vol. 176, pp. 2053-2058.
Leonard et al., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells", The Journal of Biological Chemistry, Jun. 25, 1990, vol. 265, No. 18, pp. 10373-10382.
Li et al., "Genetic and Neutralization Properties of Subtype C Human Immunodeficiency Virus Type 1 Molecular env Clones from Acute and Early Heterosexually Acquired Infections in Southern Africa", Journal of Virology, Dec. 2006, vol. 80, No. 23, pp. 11776-11790.
Li et al., "Glycosylation is Necessary for the Correct Folding of Human Immunodeficiency Virus gp120 in CD4 Binding", Journal of Virology, Jan. 1993, vol. 67, No. 1, pp. 584-588.
Li et al., "Human Immunodeficiency Virus Type 1 env Clones from Acute and Early Subtype B Infections for Standardized Assessments of Vaccine-Elicited Neutralizing Antibodies", Journal of Virology, Aug. 2005, vol. 79, No. 16, pp. 10108-10125.
Low et al., "Oral and pulmonary delivery of FSH-Fc fusion proteins via neonatal Fc receptor-mediated transcytosis", Human Reproduction, 2005, vol. 20, No. 7, pp. 1805-1813.
Malenbaum et al., "The N-Terminal V3 Loop Glycan Modulates the Interaction of Clade A and B Human Immunodeficiency Virus Type 1 Envelopes with CD4 and Chemokine Receptors", Journal of Virology, Dec. 2000, vol. 74, No. 23, pp. 11008-11016.
Mariner et al., "The HIV-Inactivating Protein, Cyanovirin-N, Does Not Block gp120-Mediated Virus-to-Cell Binding", Biochemical and Biophysical Research Communications, 1998, vol. 248, pp. 841-845.
Matei et al., "Solution and Crystal Structures of a Sugar Binding Site Mutant of Cyanovirin-N: No Evidence of Domain Swapping", Structure, Aug. 6, 2008, vol. 16, pp. 1183-1194.
McCoy et al., "Likelihood-enhanced fast translation functions", Acta Cryst., 2005, vol. D61, pp. 458-464.
McFadden et al., "A Recombinant Allosteric Lectin Antagonist of HIV-1 Envelope gp120 Interactions", Proteins: Structure, Function, and Bioinformatics, 2007, vol. 67, pp. 617-629.

Michelow et al., "A Novel L-ficolin/Mannose-binding Lectin Chimeric Molecule with Enhanced Activity against Ebola Virus", The Journal of Biological Chemistry, Aug. 6, 2010, vol. 285, No. 32, pp. 24729-24739.
Montefiori et al., "Role of protein N-glycosylation in pathogenesis of human immunodeficiency virus type 1", Proc. Natl. Acad. Sci. USA, Dec. 1998, vol. 85, pp. 9248-9252.
Mori et al., "Analysis of Sequence Requirements for Biological Activity of Cyanovirin-N, a Potent HIV (Human Immunodeficiency Virus)-Inactivating Protein", Biochemical and Biophysical Research Communications, 1997, vol. 238, pp. 218-222.
Mori et al., "Construction and Enhanced Cytotoxicity of a [Cyanovirin-N]-[Pseudomonas Exotoxin] Conjugate against Human Immunodeficiency Virus-Infected Cells", Biochemical and Biophysical Research Communications, 1997, vol. 239, pp. 884-888.
Mori et al., "Cyanovirin-N, a Potent Human Immunodeficiency Virus-Inactivating Protein, Blocks both CD4-Dependent and CD4-Independent Binding of Soluble gp120 (sgp120) to Target Cells, Inhibits sCD4-Induced Binding of sgp120 to Cell-Associated CXCR4, and Dissociates", Bound sgp120 from Target Cells Antimicrobial Agents and Chemotherapy, Mar. 2001, vol. 45, No. 3, pp. 664-672.
Mori et al., "Functional homologs of cyanovirin-N amenable to mass production in prokaryotic and eukaryotic hosts", Protein Expression and Purification, 2002, vol. 26, pp. 42-49.
Mori et al., "Recombinant Production of Cyanovirin-N, a Potent Human Immunodeficiency Virus-Inactivating Protein Derived from a Cultured Cyanobacterium", Protein Expression and Purification, 1998, vol. 12, pp. 151-158.
Mossad, "Influenza update 2007-2008: Vaccine advances, pandemic preparation", Cleveland Clinic Journal of Medicine, Dec. 2007, vol. 74, No. 12, pp. 889-894.
Murshudov et al., "Refinement of Macromolecular Structures by the Maximum-Likelihood Method", Acta Cryst., 1997, vol. D53, pp. 240-255.
Nishi et al., "Development of highly stable galectins: Truncation of the linker peptide confers protease-resistance on tandem-repeat type galectins", FEBS Letters, 2005, vol. 579, pp. 2058-2064.
Ofek et al., "Structure and Mechanistic Analysis of the Anti-Human Immunodeficiency Virus Type 1 Antibody 2F5 in Complex with Its gp41 Epitope", Journal of Virology, Oct. 2004, vol. 78, No. 19, pp. 10724-10737.
O'Keefe et al., "Analysis of the Interaction between the HIV-Inactivating Protein Cyanovirin-N and Soluble Forms of the Envelope Glycoproteins gp120 and gp41", Mol Pharmacol, 2000, vol. 58, No. 5, pp. 982-992.
Sjolander et al., "N-Linked Glycans in the CD4-Binding Domain of Human Immunodeficiency Virus Type 1 Envelope Glycoprotein gp160 Are Essential for the in Vivo Priming of T Cells Recognizing an Epitope Located in Their Vicinity", Virology, 1996, vol. 215, pp. 124-133.
Smee et al., "Influenza A (H1N1) virus resistance to cyanovirin-N arises naturally during adaptation to mice and by passage in cell culture in the presence of the inhibitor", Antiviral Chemistry & Chemotherapy, Dec. 10, 2007, vol. 18, pp. 317-327.
Smee et al., "Treatment of influenza A (H1N1) virus infections in mice and ferrets with cyanovirin-N", Antiviral Research, 2008, vol. 80, pp. 266-271.
Stabila et al., "Cell surface expression of a human IgG Fc chimera activates macrophages through Fc receptors", Nature Biotechnology, Dec. 1998, vol. 16, pp. 1357-1360.
Stemmer et al., "Single-step assembly of a gene and entire plasmid from large numbers of oligodeoxyribonucleotides", Gene, 1995, vol. 164, pp. 49-53.
Sugrue, "Viruses and Glycosylation", Methods in Molecular Biology, Glycovirology Protocols, pp. 1-13, 2007.
Sugrue et al., "Antiviral Drugs for the Control of Pandemic Influenza Virus", Ann Acad Med Singapore, 2008, vol. 37, pp. 518-524.
Tosh et al., "Flu Myths: Dispelling the Myths Associated With Live Attenuated Influenza Vaccine", Mayo Clin Proc., Jan. 2008, vol. 83, No. 1, pp. 77-84.

(56) References Cited

OTHER PUBLICATIONS

Traggiai et al., "Development of a Human Adaptive Immune System in Cord Blood Cell-Transplanted Mice", Science, Apr. 2, 2004, vol. 304, pp. 104-107.

Trkola et al., "Cross-Clade Neutralization of Primary Isolates of Human Immunodeficiency Virus Type 1 by Human Monoclonal Antibodies and Tetrameric CD4-IgG", Journal of Virology, Nov. 1995, vol. 69, No. 11, pp. 6609-6617.

Trkola et al., "Human Monoclonal Antibody 2G12 Defines a Distinctive Neutralization Epitope on the gp120 Glycoprotein of Human Immunodeficiency Virus Type 1", Journal of Virology, Feb. 1996, vol. 70, No. 2, pp. 1100-1108.

Tsai et al., "Cyanovirin-N Gel as a Topical Microbicide Prevents Rectal Transmission of SHIV89.6P in Macaques", AIDS Research and Human Retroviruses, 2003, vol. 19, No. 7, pp. 535-541.

Tsai et al., "Cyanovirin-N Inhibits Aids Virus Infections in Vaginal Transmission Models", AIDS Research and Human Retroviruses, 2004, vol. 20, No. 1, pp. 11-18.

Vigerust et al., "Virus glycosylation: role in virulence and immune interactions", Trends in Microbiology, 2007, vol. 15, No. 5, pp. 211-218.

Von Itzstein, "Avian influenza virus, a very sticky situation", Chemical Biology, 2008, vol. 12, pp. 102-108.

Webby et al., "Are We Ready for Pandemic Influenza?", Science, Nov. 28, 2003, vol. 302, pp. 1519-1522.

Wei et al., "Antibody neutralization and escape by HIV-1", Nature, Mar. 20, 2003, vol. 422, pp. 307-312.

Weingarten et al., "Barriers to influenza vaccine acceptance A survey of physicians and nurses", Am J Infect Control, Aug. 1989, vol. 17, No. 4, pp. 202-207.

Weis et al., "The C-type lectin superfamily in the immune system", Immunological Reviews, 1998, vol. 163, pp. 19-34.

West, Jr. et al., "Design and Expression of a Dimeric Form of Human Immunodeficiency Virus Type 1 Antibody 2G12 with Increased Neutralization Potency", Journal of Virology, Jan. 2009, vol. 83, No. 1, pp. 98-104.

Wolbank et al., "Characterization of Human Class-Switched Polymeric (Immunoglobulin M [IgM] and IgA) Anti-Human Immunodeficiency Virus Type 1 Antibodies 2F5 and 2G12", Journal of Virology, Apr. 2003, vol. 77, No. 7, pp. 4095-4103.

Yang et al., "Crystal Structure of Cyanovirin-N, a Potent HIV-inactivating Protein, Shows Unexpected Domain Swapping", J. Mol. Biol., 1999, vol. 288, pp. 403-412.

Zappe et al., "PEGylation of cyanovirin-N, an entry inhibitor of HIV", Advanced Drug Delivery Reviews, 2008, vol. 60, pp. 79-87.

Zhang et al., "HIV-1 infection and pathogenesis in a novel humanized mouse model", Blood, Apr. 1, 2007, vol. 109, No. 7, pp. 2978-2981.

Zhou et al., "Structural definition of a conserved neutralization epitope on HIV-1 gp120", Nature, Feb. 15, 2007, vol. 445, pp. 732-737.

Zhu et al., "Distribution and three-dimensional structure of AIDS virus envelope spikes", Nature, Jun. 15, 2006, vol. 441, pp. 847-852.

D

E

SEQUENCE LISTING

<160> NUMBER OF SEQ IDS NOS: 7

<210> SEQ ID NO 1
<211> LENGTH: 18
<212> TYPE: DNA
<213> ORGANISM: Artificial Sequence
<220> FEATURE:
<223> OTHER INFORMATION: synthetically produced sequence

<400> SEQUENCE: 1
ctatcatcac acatctat                                              18

<210> SEQ ID NO 2
<211> LENGTH: 18
<212> TYPE: DNA
<213> ORGANISM: Artificial Sequence
<220> FEATURE:
<223> OTHER INFORMATION: synthetically produced sequence

<400> SEQUENCE: 2
acaaccactt acttcttc                                              18

<210> SEQ ID NO 3
<211> LENGTH: 14
<212> TYPE: DNA
<213> ORGANISM: Artificial Sequence
<220> FEATURE:
<223> OTHER INFORMATION: synthetically produced sequence

<400> SEQUENCE: 3
acaaccactt actt                                                  14

<210> SEQ ID NO 4
<211> LENGTH: 18
<212> TYPE: DNA
<213> ORGANISM: Artificial Sequence
<220> FEATURE:
<223> OTHER INFORMATION: synthetically produced sequence

<400> SEQUENCE: 4
ctatacaacc acttactt                                              18

<210> SEQ ID NO 5
<211> LENGTH: 18
<212> TYPE: DNA
<213> ORGANISM: Artificial Sequence
<220> FEATURE:
<223> OTHER INFORMATION: synthetically produced sequence

<400> SEQUENCE: 5
gccatcagga cttaacct                                              18

<210> SEQ ID NO 6
<211> LENGTH: 10
<212> TYPE: DNA
<213> ORGANISM: Artificial Sequence
<220> FEATURE:
<223> OTHER INFORMATION: synthetically produced sequence

<400> SEQUENCE: 6
ctttcctaca                                                       10

<210> SEQ ID NO 7
<211> LENGTH: 10
<212> TYPE: DNA
<213> ORGANISM: Artificial Sequence

```
<220> FEATURE:
<223> OTHER INFORMATION: synthetically produced sequence

<400> SEQUENCE: 7
cctacgtctc                                                                 10
```

METHOD AND MATERIALS FOR THE COOPERATIVE HYBRIDIZATION OF OLIGONUCLEOTIDES

CROSS-REFERENCE TO RELATED APPLICATIONS

The current application claims priority to U.S. Provisional App. No. 61/315,279, filed Mar. 18, 2010, the disclosure of which is incorporated herein by reference.

STATEMENT OF FEDERAL FUNDING

The federal government has rights to current invention pursuant to a funding provided in accordance with Grant No. CCF0728703, awarded by National Science Foundation

FIELD OF THE INVENTION

The current invention is generally directed to methods and molecules for reacting and co-localizing a plurality target oligonucleotides and more particularly, to a generalized method for implementing cooperative hybridization of oligonucleotides of independent sequence simultaneously and cooperatively through a two-stranded intermediary complex.

BACKGROUND OF THE INVENTION

The precise temporal and spatial control of molecules is a fundamental goal of both synthetic biology and nanotechnology, and is essential for building reliable nanoscale structures and devices. Nucleic acids, by virtue of their well-understood hybridization thermodynamics and kinetics, exponential information content and 0.4 nm addressability, and economy of synthesis and preparation, have emerged as a leading material for nanoscale engineering. (See, e.g., SantaLucia, J. & Hicks, D., *Annu. Rev. Biochem.* 2004, 33, 415-440; Bloomfield, V. A, et al., *Nucleic Acids: Structures, Properties, and Functions*, University Science Books: Sausalito, Calif., 2000; Carlson, R., *Nat. Biotechnol.* 2009, 27, 1091-1094; Aldaye, F. A., *Science* 2008, 321, 1795-1799; Shih, W. M. & Lin, C., *Curr. Opin. Struct. Biol.* 2010, 20, 276-282; Lu, Y. & Liu, J., *Curr. Opin. Biotechnol.* 2006, 17, 580-588; Willner, I., et al., *Chem. Soc. Rev.* 2008, 37, 1153-1165; Bath, J. & Turberfield, A. J., *Nature Nanotechnol.* 2007, 2, 275-284; and Zhang, D. Y. & Seelig, G., *Nature Chem.* 2010, DOI: 10.1038/NCHEM.957, the disclosures of each of which are incorporated herein by reference.) Furthermore, the biological relevance of nucleic acids and the ease of coupling nucleic acids to other materials, such as proteins and carbon nanotubes, facilitate the use of nucleic acids both as synthetic biomaterials and as scaffolds for other nanotechnological applications. (See, e.g., Bartel, D. P., *Cell* 2009, 136, 215-233; Lu, J., et al., *Nature* 2005, 435, 834-838; Rinker, S., et al, *Nature Nanotechnol.* 2008, 3, 418-422; Maune, H. T., et al., *Nature Nanotechnol.* 2010, 5, 61-66, the disclosures of each of which are incorporated herein by reference.)

Although the first generation of DNA nanotechnology research has focused on the self-assembly of static DNA nanostructures, recent works in the field have also expanded into the realm of constructing dynamic nucleic acid devices, in which nucleic acid nanostructures conditionally and programmably reconfigure in solution. (See, e.g., Bath, J. & Turberfield, A. J., *Nature Nanotechnol.* 2007, 2, 275-284; Zhang, D. Y. & Seelig, G., *Nature Chem.* 2010, 103-113; Winfree, E., et al., *Nature* 1998, 394, 539-544; Rothemund, P. W. K, et al., *Plos Biol.* 2004, 2, 2041-2053; Rothemund, P. W. K., *Nature* 2006, 440, 297-302; Douglas, S. M., et al., *Nature* 2009, 459, 414-418; and Zheng, J., et al., *Nature* 2009, 461, 74-77, the disclosures of each of which are incorporated herein by reference.) Examples include cascaded logical and amplification circuits, DNA origami boxes that close and open, molecular walkers that traverse predefined landscapes, controlled rotating DNA frameworks, and chain reaction DNA motors and dendrimers. (See, e.g., Stojanovic, M. N. & Stefanovic, D., *Nat. Biotechnol.* 2003, 21, 1069-1074; Lederman, H., et al., *Biochemistry* 2006, 45, 1194-1199; Win, M. N. & Smolke, C. D., *Science* 2008, 322, 456-460; Levy, M. & Ellington, A. D., *Proc. Natl. Acad. Sci. U.S.A.* 2003, 100, 6416-6421; Seelig, G., et al., *Science* 2006, 314, 1585-1588; Seelig, G., et al., *Am. Chem. Soc.* 2006, 128, 12211-12220; Zhang, D. Y., et al., *Science* 2007, 318, 1121-1125; Frezza, B. M., et al., *J. Am. Chem. Soc.* 2007, 129, 14875-14879; Zhang, D. Y. & Winfree, E., *J. Am. Chem. Soc.* 2008, 130, 13921-13926; Andersen, E. S., et al., *Nature* 2009, 459, 73-76; Pei, R., et al., *J. Am. Chem. Soc.* 2006, 128, 12693-12699; Lund, K., et al., *Nature* 2010, 465, 206-210; Omabegho, T., et al., *Science* 2009, 324, 67-71; Green, S., et al., *Phys. Rev. Lett.* 2008, 101, 238101; Yurke, B., et al., *Nature* 2000, 406, 605-608; Yan, H., et al., *Nature* 2002, 415, 62-65; Gu, H., et al., *Nature* 2010, 465, 202-205; Dirks, R. M. & Pierce, N. A., *Proc. Natl. Acad. Sci. U.S.A.* 2004, 101, 15275-1278; Venkataraman, S., et al., *Nature Nanotechnol.* 2007, 2, 490-494; and Yin, P., et al., *Nature* 2008, 451, 318-322, the disclosures of each of which are incorporated herein by reference.)

While some of the above constructions relied on functional nucleic acid molecules with innate catalytic activity (known as ribozymes and deoxyribozymes, see above citations), many others were constructed using purely rational design approaches, based on the well-characterized thermodynamic and kinetic properties of DNA hybridization, branch migration, and dissociation processes. (See, e.g., Dirks, R. M., et al., *SIAM Rev.* 2007, 49, 65-88; Zhang, D. Y. & Winfree, E., *J. Am. Chem. Soc.* 2009, 131, 17303-17314; and Yurke, B. & Mills, A. P., *Genet. Programming Evolvable Machines* 2003, 4, 111-122, the disclosures of each of which are incorporated herein by reference.) The latter group generally relies the clever and repeated use of a simple but reliable mechanism, known as toehold-mediated strand displacement, in which short, single-stranded domains on different DNA molecules hybridize to colocalize the molecules, enabling subsequent branch migration. (See, e.g., Zhang, D. Y. & Seelig, G., *Nature Chem.* 2010; and Yurke, B., et al., *Nature* 2000, cited above.) To further expand the scope of functions achievable with dynamic DNA nanotechnology, it is necessary to develop other molecular mechanisms that afford functionality that toehold-mediated strand displacement cannot achieve.

SUMMARY OF THE INVENTION

The current invention is directed generally to a cooperative hybridization system and method.

In one embodiment, the system includes:
A plurality of target oligonucleotide strands of one of either identical or independent sequence; and
a multi-stranded DNA intermediary complex having independent binding domain regions that are complementary to the target oligonucleotides for reversibly binding the oligonucleotide strands;
In one such embodiment, each of the binding domain regions of the intermediary complex are formed from a plurality of individual domains. In another such embodiment, the binding domain regions are adjacent such that when hybridized the target oligonucleotide strands are co-localized.

In another embodiment, the hybridization of less than all of the target oligonucleotides to the substrate strand of the intermediary complex only partially and reversibly displaces the protector strand, while the hybridization of all the target oligonucleotides to the substrate strand irreversibly releases the protector strand from said substrate strand, and produces a dual-hybridized product including the target oligonucleotides and substrate strand. In such an embodiment, the number of oligonucleotides may be two or more.

In still another embodiment, the equilibrium distribution between the target oligonucleotides and intermediary complex collectively, and the dual-hybridized product and protector strand collectively is concentration dependent. In one such embodiment, at low concentrations the target oligonucleotides and intermediary complex are favored, while at high concentrations the dual-hybridized product and protector strand are favored.

In yet another embodiment, the individual reaction of less than all of the target oligonucleotides with the intermediary complex is thermodynamically unfavorable. In such an embodiment, the individual hybridization energies of the target oligonucleotides is insufficient to overcome the entropic loss of co-localizing less than all of the target oligonucleotides with the intermediary complex, while the collective hybridization energies of all of the target oligonucleotides is sufficient to overcome the configuration entropy loss of co-localizing the two target nucleotides to the intermediary complex.

In still yet another embodiment, the length of the protector strand is sufficiently long to prevent spontaneous dissociation thereof from said substrate strand.

In still yet another embodiment, the lengths of the binding domains of the substrate strand is between 2 and 20 nucleotides.

In still yet another embodiment, the target oligonucleotides further include at least one dangle on at least one end thereof.

In still yet another embodiment, at least one of the target oligonucleotides, the protector strand or the dual-hybridized product includes a reporter ligand that can be detected by an analytic technique. In one such embodiment, the reporter ligand is fluorescent, such as, for example, a quantum dot and/or organic fluorophores.

In still yet another embodiment, the system includes at least one additional catalyst system. In one such embodiment, the additional catalyst system includes at least one additional multi-stranded complex having substrate and reporter strands, wherein a molecule selected from the group consisting of one of the target oligonucleotides, the protector strand, and the dual-hybridized product operates as a catalyst molecule for the release of the reporter strand in the at least one additional catalyst system. In another such embodiment, any number of additional catalyst systems may be included in which the release of a product from the initial additional catalyst system acts as a catalyst for a subsequent catalyst system, such that the overall system provides one of either a cascade or a feedback function. In one such embodiment, the catalyst molecule of the first catalyst system and the catalyst molecule of the second catalytic system are binding site independent.

In still yet another embodiment, the release of the protector strand or the production of the dual-hybridized product follows a sigmoidal relationship to the concentration of one of the target oligonucleotides. In one such embodiment, the system further includes a second multi-stranded complex reactive to at least one of said target oligonucleotides, such that if the concentration of the reactive oligonucleotide is above a certain threshold the second multi-stranded will react therewith, thereby converting the linear concentration relationship of the cooperative hybridization system to a sigmoidal concentration relationship. In another such embodiment, the system is supplied with a multi-stranded precursor complex formed from the substrate strand one of the target oligonucleotides, and is reacted with the protector strand to produce an amount of the target oligonucleotide and the intermediary complex, such that when the other target oligonucleotides is added it reacts and consumes the precursor complex before reacting with any of the formed intermediary complex, thereby converting the linear concentration relationship of the cooperative hybridization system to a sigmoidal concentration relationship.

In still yet another embodiment, at least one fluorescent label is provided such that the system functions as a logic gate. In one such embodiment, the logic gate is selected from the group consisting of AND, OR and NOT.

In still yet another embodiment, the system includes a plurality of such logic gates wherein the output molecule of the logic gate serves as a catalytic input for at least one additional catalytic logic gate. In one such embodiment the first catalytic logic gate is an AND gate, and the additional catalytic logic gate is a NOT gate such that they combine to form a NAND logic gate.

In still yet another embodiment, the system includes at least three target oligonucleotides. In one such embodiment, the cooperative hybridization system comprises:
 at least three target oligonucleotide strands, being of one of either identical or independent sequence; and
 a DNA intermediary complex being composed of substrate and protector molecules, the substrate molecule having a plurality of independent binding domain regions that are complementary to the target oligonucleotides for reversibly binding said first and second target oligonucleotide molecules, each of the binding domain regions being formed from a plurality of individual domains, and said binding domain regions being joined such that when hybridized therewith the at least first and second target oligonucleotide strands are co-localized.

In another such embodiment, the hybridization of less than all of the target oligonucleotides to the substrate strand of said intermediary complex only partially and reversibly displaces the protector molecule, while the hybridization of all the target oligonucleotides to the substrate molecule irreversibly releases said protector molecule from said substrate molecule, and produces a dual-hybridized product including the target oligonucleotides and the substrate molecule. In still another such embodiment, at least one of the protector or substrate molecule is one of either a multi-stranded complex or a branched nucleic acid oligonucleotide. In such an embodiment, the binding regions may be joined via one of either covalent chemistry or multi-armed double-stranded nucleic acid junctions, wherein the covalent chemistry is at least one technique selected from custom branched oligonucleotides and non-specifically cross-linked DNA oligonucleotides, wherein the non-specifically cross-linked DNA oligonucleotide is selected from the group consisting of formaldehyde, cisplatin, psoralens, and nitrous acid.

In still yet another embodiment, the oligonucleotides are attached to DNA nanostructures, and wherein the intermediary complex is a freely diffusing two-stranded linker complex to link said DNA nanostructures.

In another embodiment, the invention is directed to a method of cooperatively hybridizing at least two target oligonucleotide strands.

In one such embodiment, the method includes:
providing a number of target oligonucleotide strands of identical or independent sequence;
providing a multi-stranded DNA intermediary complex having independent binding domain regions that are complementary to the target oligonucleotides for reversibly binding the oligonucleotide strands, where the binding domain regions are adjacent such that when hybridized therewith the first and second target oligonucleotide strands are co-localized; and In one embodiment, the method also includes monitoring the release of at least one product from the cooperative hybridization or the consumption or sequestering of at least one of the target oligonucleotides.

In one embodiment the hybridization of less than all of the target oligonucleotides to the substrate strand only partially and reversibly displaces the protector strand, while the hybridization of all the target oligonucleotides to the substrate strand irreversibly releases the protector strand from the substrate strand, and produces a dual-hybridized product including the oligonucleotides and substrate strand.

In another embodiment, the target oligonucleotides are a synthetic or naturally occurring DNA or RNA molecule. In such an embodiment the monitoring of the concentration of the target oligonucleotides could be based on the rate of production of the dual-hybridized product to provide real-time detection and quantitation of DNA and RNA concentrations in the system.

In yet another embodiment, the individual reaction of less than all of the target oligonucleotides with the intermediary complex is thermodynamically unfavorable. In such an embodiment, the individual reaction of one or less than all of the target oligonucleotides with the intermediary complex is thermodynamically unfavorable, while the collective hybridization energies of the target oligonucleotides is sufficient to overcome the configuration entropy loss of co-localizing the target nucleotides to the intermediary complex.

In still another embodiment, the method includes providing a known concentration of the one target oligonucleotide and an excess concentration of the intermediary complex are provided, and monitoring the stoichiometric consumption of a second target oligonucleotide to determine the concentration thereof.

In still yet another embodiment, at least one of the protector strand the dual-hybridized product or the target oligonucleotides includes a reporter ligand that can be detected by an analytic technique.

In still yet another embodiment, the method includes adding at least one additional catalyst system, such as, for example, a multi-stranded complex having substrate and reporter strands, where a molecule selected from the group consisting of one of the target oligonucleotides, the protector strand, and the dual-hybridized product operates as a catalyst molecule for the release of the reporter strand in the at least one additional catalyst system.

In still yet another embodiment, the method includes adding a plurality of additional multi-stranded complexes in which the release of a product from the initial additional multi-stranded complex acts as a catalyst for a subsequent multi-stranded complex, such that the overall system provides one of either a cascade or a feedback function. In one such embodiment, the method also includes providing a second multi-strand complex formed from the substrate strand of the intermediary complex and one of the two target oligonucleotides, and reacting it with the protector strand to produce an amount of the target oligonucleotide and the intermediary complex, such that when the other target oligonucleotides are added they react and consume the precursor complex before reacting with any of the formed intermediary complex, thereby converting the linear concentration relationship of the cooperative hybridization system to a sigmoidal concentration relationship.

In still yet another embodiment, the system and method include the two target oligonucleotides that are identical in sequence, such that there exists only one unique target oligonucleotide, and such that the release of product and the production of the dual-hybridized product will both follow a sigmoidal relation with the concentration of the target.

BRIEF DESCRIPTION OF THE DRAWINGS

These and other features and advantages of the present invention will be better understood by reference to the following detailed description when considered in conjunction with the accompanying data, wherein.

Figure 6:
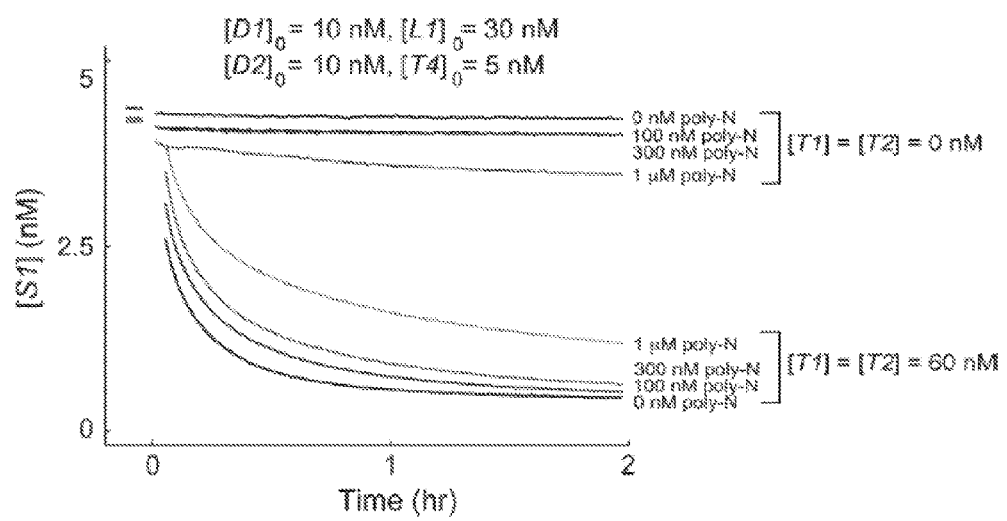
Figure 7:
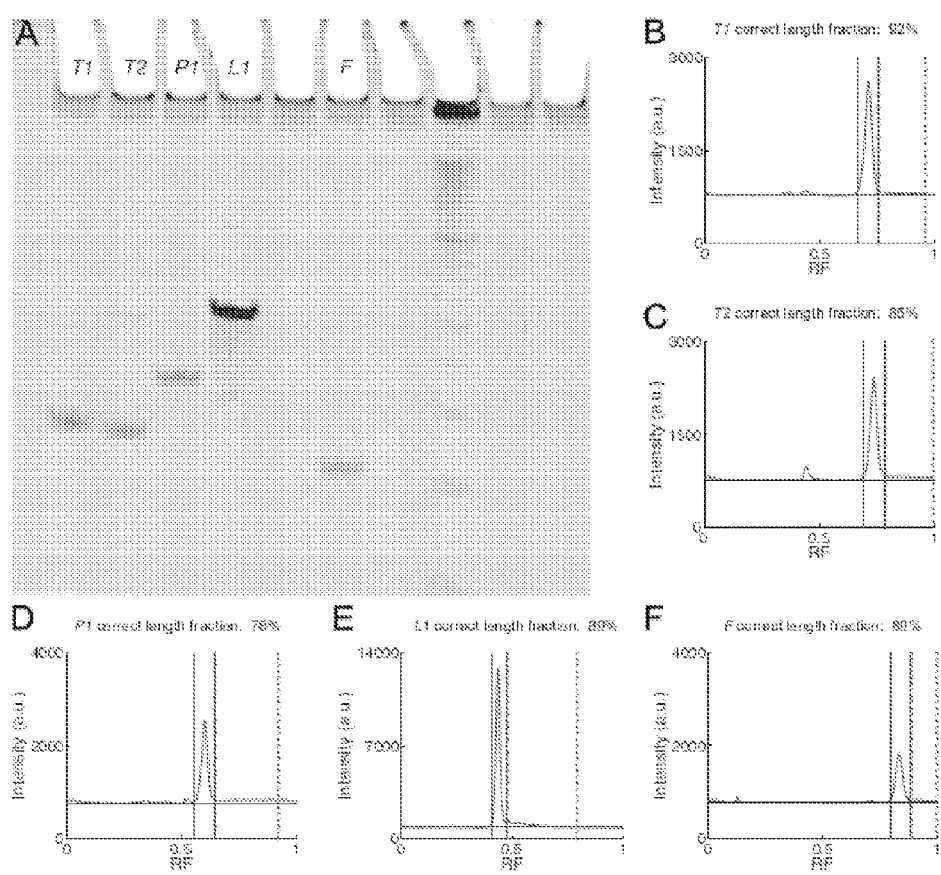
Figure 8:
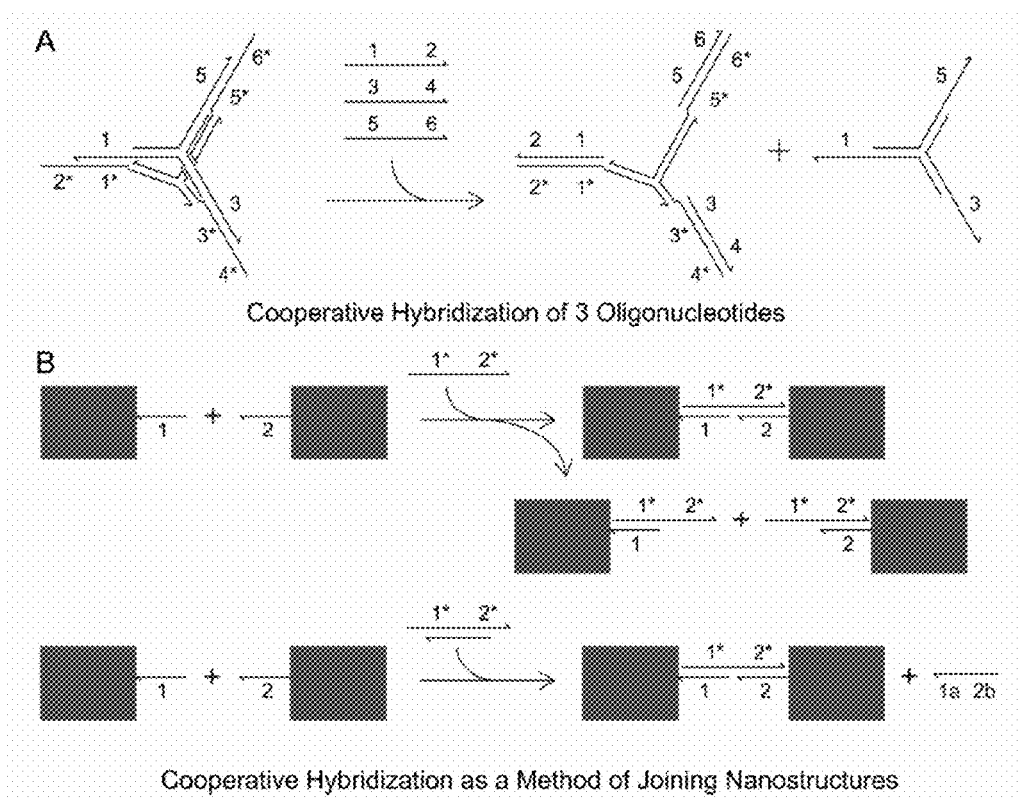
Figure 8C:
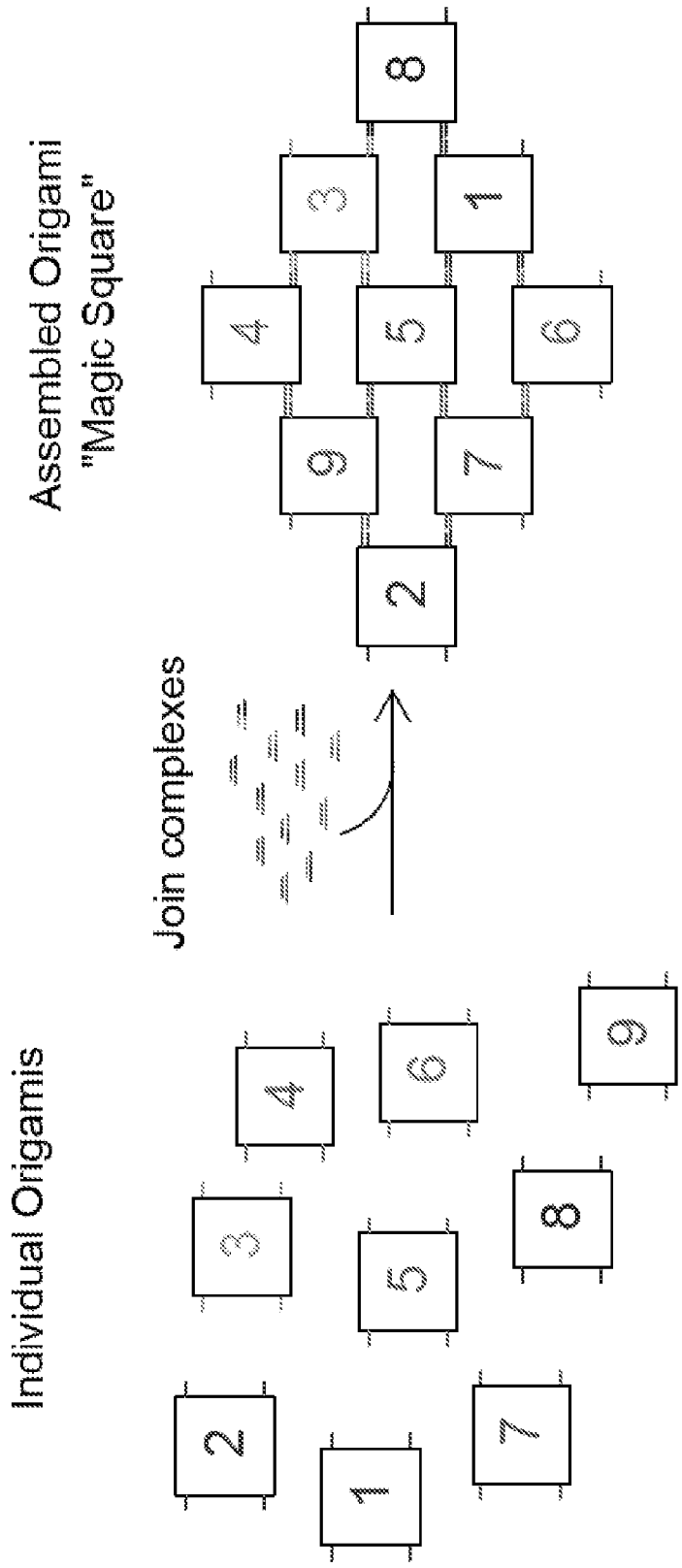

FIG. $2D_{1-4}$ provides data plots showing rate constant characterization, wherein the dotted lines show the simulations of the reaction given the listed concentrations and the fitted rate constant when Reporter R was present in the cuvette initially, and various amounts of P1 were added at t≈0, where: (1) shows a $k_{rep}=1.3 \cdot 10^7 \text{ M}^{-1}\text{s}^{-1}$, (2) shows the rate constant $k_{f1}$ fitted by observing the kinetics of the J+T1→P1+H1 reaction using the fitted $k_{rep}$ from (1), (3) shows the rate constant $k_{f2}$ fitted by pre-reacting D1 and T1 to form I, (4) shows the rate constants $k_{r1}$ and $k_{r2}$ fitted simultaneously using the results of the full system shown in FIG. 2A and simulations of the reactions in (2) and (3) including the reverse reactions;

FIG. $2E_{1-4}$ provides data plots showing concentration inference from the data in FIG. 2B, each sub-figure shows two linear fits, one to the first 4 data points and one to the last 4 data points (other than the 150 μL), where the intersection of the two linear fits is the inferred matching volume of T3, the volume of T3 in which the quantity of T3 and T4 are stoichiometrically balanced;

FIGS. 3A to 3D provide schematics (A), and data plots (B to D) summarizing studies demonstrating the cooperativity of the method in accordance with an exemplary embodiment of the invention;

FIGS. 4A to 4C provide schematics (A), and data plots (B to D) of the amplified digital detection of over- and under-expression relative to a threshold in accordance with an exemplary embodiment of the invention;

FIGS. 4D & 4E provide schematic (D) and data plot (E) for a digital concentration comparison where a standard complex M is pre-reacted with a small quantity of P1 to generate an equal small quantity of D1 and T2;

FIGS. 5A to 5E provide schematics (A & C), and data plots (B, D & E) of cascaded nucleic acid logic in accordance with an exemplary embodiment of the invention;

FIG. 6 provides a data plot showing the robustness to background molecules in accordance with an exemplary embodiment of the invention;

FIGS. 7A to 7F provide data images and graphs showing the characterization of impurities present in the oligonucleotide samples, where the trace shows the gel intensity against the relative front (RF), the solid line shows the inferred background intensity, calculated from averaging the intensities between RF=0.2 and 0.3, and the area between the solid vertical lines and above the background are assumed to be the correct length product, and the area between the dotted vertical lines and above the background are assumed to be truncation products; and FIGS. 8A to 8C provide schematics of potential extensions of cooperative hybridization in accordance with an exemplary embodiment of the invention.

DETAILED DESCRIPTION OF THE INVENTION

The current invention is directed to a generalized method for implementing cooperative hybridization in which multiple oligonucleotides (targets) of independent sequence simultaneously and cooperatively bind to a designed two-stranded complex. The complex allows the targets to stoichiometrically react and colocalize with each other, much in the same way that complementary oligonucleotides hybridize to each other.

Background on Nucleotide Reactions

It is well accepted that nucleic acids play key roles in many facets of biology, acting as regulatory signals as well as information storage media. At the same time, nucleic acids have been shown to be prime nanoscale engineering materials with the rational construction of nucleic acid-based structures, motors, and circuits. There are three main reasons for the rise of nucleic acids as the biomolecular engineering materials of choice. First, advances in efficient synthesis of oligonucleotides has improved availability of these materials. (See, e.g., R. Carlson, Nat. Biotech. 2009, 27, 1091, the disclosure of which is incorporated herein by reference.) Second, nucleic acid structure, folding, and interactions are easy to predict because they are mostly determined by Watson-Crick base pairing. (See, e.g., V. A. Bloomfield, D. M. Crothers, I. Tinoco, I. Jr., Nucleic Acids: Structures, Properties, and Functions University Science Books, Sausalito, Calif., 2000, the disclosure of which is incorporated herein by reference.) Third, the biological role of nucleic acids has been discovered to be increasingly complex, serving to regulate gene expression as well as to encode proteins. (See, e.g., D. P. Bartel, Cell 2009, 136, 215; A. L. Gartel & E. S. Kandel, Biomolecular Engineering 2006, 23, 17; A. J. Hamilton & D. C. Baulcombe, Science 1999, 286, 950; and P. D. Zamore, et al., Cell 2000, 101, 25, the disclosures of each of which are incorporated herein by reference.)

Some of the greatest accomplishments of nucleic acid biomolecular engineering in recent years have been the development of ever-more reliable self-assembly, resulting in the construction of 2- and 3-dimensional structures of up to 200 microns on a side. (See, e.g., E. Winfree, et al., Nature 1998, 394, 539; P. Rothemund, Nature 2006, 440, 297; S. M. Douglas et al., Nature 2009, 459, 414; and J. Zheng et al., Nature 2009, 461, 74, the disclosures of each of which are incorporated herein by reference.) Simultaneously, there is burgeoning interest in dynamical DNA reactions and networks, in which DNA strands can be programmed to reconfigure themselves for evaluating biomolecular logic, performing physical work or controlling self-assembly. (See, e.g., D. Y. Zhang, et al., Science 2007, 318, 1121; G. Seelig, et al., Science 2006, 314, 1585; B. M. Frezza, et al., J. Am. Chem. Soc. 2007, 129, 14875; M. N. Win & C. D. Smolke, Science 2008, 322, 456; Z. Xie, et al., Nuc. Acids Res. 2010, 38(8), 2702-11; B. Yurke, et al., Nature 2000, 406, 605; S. Green, et al., Phys. Rev. Lett. 2008, 101, 238101; T. Omabegho, et al., Science 2009, 324, 67; C. Mao, et al., Nature 1999, 397, 144; B. Ding & N. C. Seeman, Science 314, 1583 (2006); R. M. Dirks & N. A. Pierce, Proc. Nat. Acad. Sci. 2004, 101, 15275; and P. Yin, et al., Nature 2008, 451, 318, the disclosures of each of which are incorporated herein by reference.)

One frequently used mechanism for constructing DNA devices with dynamic behavior is strand displacement, in which a single-stranded DNA molecule (strand) reacts with a multi-stranded DNA complex to stoichiometrically release another DNA strand. (See, citations above.) The kinetics of strand displacement can be designed and predicted based on the thermodynamics of the involved strands, with rate constants ranging 6 orders of magnitude. (See, e.g., D. Y. Zhang & E. Winfree, J. Am. Chem. Soc. 2009, 131, 17303, the disclosure of which is incorporated herein by reference.) By designing cascades of strand displacement reactions in which products of certain reactions serve as the reactants of others, one can program complex reaction networks with fine control over the timing and release of synthetic nucleic acid molecules. Strand displacement cascades, however, are inherently serial molecular process, and do not readily allow the design of simultaneous biomolecular events.

The Inventive Cooperative Hybridization Mechanism

Here, a novel cooperative hybridization mechanism is presented that enables the construction of dynamic DNA devices with simultaneity detection, precise timing control, and non-linear signal responses. As examples, cascaded circuits capable of performing nucleic acid quantitation, detection, and logical evaluation are provided in the exemplary embodiments, below. Designs based on cooperative strand displacement are promising alternatives to molecular beacon, qPCR, and conventional strand displacement-based methods for processing short oligonucleotides because of their accuracy, robustness, modularity, and low equipment cost.

In contrast to toehold-mediated strand displacement reaction networks, which primarily rely on sequential hybridization and branch migration events, cooperative hybridization enables parallel hybridization and branch migration events to occur. In addition to enabling networks, such as amplified digital detection of over- and under expression relative to a threshold, cooperative hybridization also offers the practical advantage of being robust to synthesis impurities and a background of unrelated nucleic acids and thus is likely to be a useful tool for engineering dynamic DNA nanotechnological devices.

Figure 1:
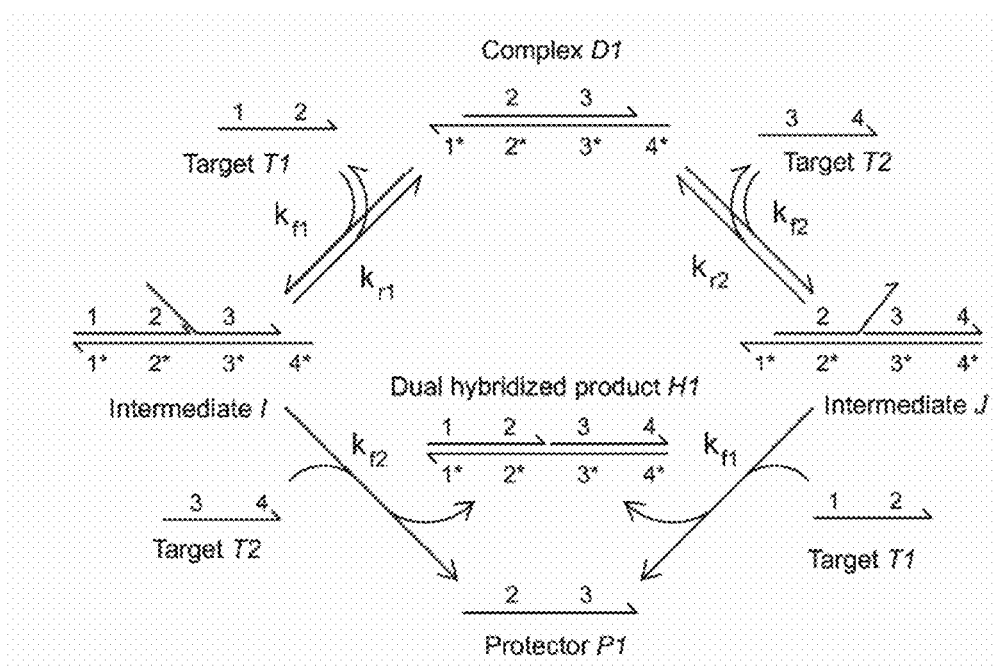
FIG. 1 provides a schematic diagram of the cooperative hybridization mechanism of the current invention, in this figure, DNA strands are represented as directional lines, with the hook denoting the 3' end, in turn, each strand is subdivided into domains, continuous nucleotides that act as a unit in hybridization, branch migration, or dissociation, and these domains are represented by numbers, and starred domains denote complements of the unstarred domains (e.g., 2* is complementary to 2)

An exemplary cooperative hybridization mechanism for a two target oligonucleotide case in accordance with the current invention is shown in FIG. 1. As shown, each of two DNA strands of interest, targets T1 and T2, bind reversibly to a 2-stranded intermediary DNA complex D1. The intermediary complex D1 is composed of upper "protector" strand P1 and lower "substrate" strand L1. The protector P1 and substrate L1 strands are both composed of independent binding domain regions that are complementary to the target oligonucleotides of interest. The constructions and characteristics of these domains will be described in greater detail in the exemplary embodiments, below.

When both the target strands, T1 and T2, are present, they hybridize simultaneously to two-stranded complex D1. There are two parallel pathways for this reaction. In one, T1 first binds to D1 to form intermediate I, which then reacts with T2 to form H1 and release product or protector strand P1. In the other pathway, T2 binds first to D1 to form intermediate J. Individually, the hybridization of T1 or T2 to D1 is reversible and thermodynamically unfavorable; the release of product P1 upon the simultaneous hybridization of T1 and T2 facilitates the net reaction. In other words, the two nucleic acid molecules T1 and T2 individually bind to D1 in a reversible manner, but their simultaneous binding releases protector strand P1 and dual-hybridized product H1, rendering the reaction irreversible.

The cooperative hybridization mechanism can be expressed as the following reactions:

$$T1+D1 \leftrightarrows I$$

$$T2+D1 \leftrightarrows J$$

$$T2+I \rightarrow P1+H1$$

$$T1+J \rightarrow P1+H1$$

The net reaction of the system is thus:

$$T1+T2+D1 \rightarrow P1+H1$$

There are three prominent features of this inventive system. First, the net reaction possesses different numbers of reactants and products, making the equilibrium distribution of the reactants and products concentration dependent. At low concentrations, entropy is a larger factor, and reactants will exist at higher concentration at equilibrium, while the opposite is true at high concentrations. At operational conditions, the products are designed to be predominant.

Second, at operational concentrations where the products are favored. In other words, in the example above, the equilibrium concentration of P1 will be roughly the minimum of the initial concentrations of T1, T2, and D1. As P1 is a strand with a different sequence than both T1 and T2, it can potentially participate in downstream reactions that T1 and T2 cannot. Thus, the cooperative hybridization mechanism not only allows the target oligonucleotides to be co-localized but also releases a reported oligonucleotide to signal the completion of the cooperative hybridization reaction.

Third, because the individual reaction of the target oligonucleotides with the intermediary complex is thermodynamically unfavorable, at operational concentrations very little of the oligonucleotide is sequestered in the intermediates, i.e., in the example little of T1 or T2 is sequestered in I or J if only one of T1 or T2 is present. The equilibrium concentration of free T1 or T2 in this case would be near the total concentration of T1 or T2. These properties of the cooperative hybridization process allow a variety of useful dynamic nucleic acid devices and circuits.

Although the above discussion has focused on the case where two oligonucleotides are used, it should be understood that the system can also be used with three or more oligonucleotides. In other words, enforcing the cooperative hybridization of three or more target oligonucleotides, such that the simultaneous hybridization of all targets is thermodynamically favorable, but the simultaneous hybridization of any subset of targets is thermodynamically unfavorable. In this extension of the invention, the intermediary complex is still composed of a protector (upper) and a substrate (lower) portion. However, the protector and/or the substrate may now be a multi-stranded nucleic acid complex, or a branched nucleic acid oligonucleotide.

As in the two target case, the substrate would have a number of binding domain regions, one complementary to each intended target, and these binding domain regions would be joined together to form the substrate through the use of (1) covalent chemistries or (2) multi-armed double-stranded nucleic acid junctions (such as that shown in FIG. 8A of the exemplary embodiments, below). Methods for achieving such covalent chemistries include, but are not limited to: (1) custom branched oligonucleotides such as using 5'-2' linkages, (2) non-specifically cross-linked DNA oligonucleotides such as through formaldehyde, cisplatin, psoralens, or nitrous acid. Methods for multi-armed double-stranded nucleic acid junctions rely on the specific hybridization of accessory sequences not complementary to any target sequences, that serve to co-localize the various different binding domain regions, and have been previously disclosed in the literature. (See, e.g., Yin, *Nature* 2008).

The protector, similarly, has a number of domain regions, with each partially complementary to one binding domain regions of the substrate, such that the simultaneous hybridization of all targets displaces the protector. The protector similarly requires the joining of these regions, which can also be achieved by (1) covalent chemistries or (2) multi-armed double-stranded nucleic acid junctions. The method for joining protector domain regions can but need not be the same as that of joining the binding domain regions for the substrate.

Specific examples of reactions, intermediary molecules, and applications of the cooperative hybridization system of the current invention are provided below, it should be understood that any intermediary molecule and mechanism that incorporates are utilized the generalized cooperative hybridization method described above is included within the scope of the invention.

EXEMPLARY EMBODIMENTS

In this section several examples of how the cooperative hybridization system of the invention could be implemented are provided. In addition, the performance of exemplary hybridization reactions conducted in accordance with the current invention are also provided. The person skilled in the art will recognize that additional embodiments according to the invention are contemplated as being within the scope of the foregoing generic disclosure, and no disclaimer is in any way intended by the foregoing, non-limiting examples. For example, although most of the examples show systems in which two oligonucleotides are hybridized, it will be understood that the system can be extended to higher order system, as described above and below in Example 6.

Materials and Methods

DNA Sequences and Design.

Each of the sequences used in these embodiments was designed using domain-based sequence design software. The domains (shown in Table 1, below) possess minimal secondary structure and crosstalk (binding between unrelated domains): NUPACK calculates there to be no more than four paired bases between any pair of strands at 25° C., even at 1 μM concentration. (See, Dirks, R. M., et al., *SIAM Rev.* 2007, 49, 65-88, the disclosure of which is incorporated herein by reference.) Furthermore, the minimum free energy states of every individual strand was completely unstructured ($\Delta G^0=0$). Thus, the domains used can be approximated as structure-free. Substantial secondary structure is known to slow down branch migration and interfere with hybridization. (See, e.g., Gao, Y., et al., *Nucleic Acids Res.* 2006, 34, 3370-3377, the disclosure of which is incorporated herein by reference.)

TABLE 1

Domain and Strand Sequences*

| Domain | Sequence | Length (nt) |
|---|---|---|
| 1 | 5'-CATCACTA-3' | 8 |
| 2 = 2a:2b:2c | 5'-CTATCATCACACATCTAT-3' (SEQ. ID. 1) | 18 |
| 2a | 5'-CTATCAT-3' | 7 |
| 2b | 5'-CACACAT-3' | 7 |
| 2c | 5'-CTAT-3' | 4 |
| 3 = 3a:3b | 5'-ACAACCACTTACTTCTTC-3' (SEQ. ID. 2) | 18 |
| 3a | 5'-ACAACCACTTACTT-3' (SEQ. ID. 3) | 14 |
| 3b | 3'-CTTC-3' | 4 |
| 4 | 5'-ATCTATCC-3' | 8 |
| 5 | 5'-CTATCAT-3' | 7 |
| 6 | 5'-CACACAT-3' | 7 |
| 7 | 5'-CTATACAACCACTTACTT-3' (SEQ. ID. 4) | 18 |
| 8 | 5'-CTTC-3' | 4 |
| 9 | 5'-GCCATCAGAACTTAACCT-3' (SEQ. ID. 5) | 18 |
| 10 | 5'-AACTC-3' | 5 |
| 11 | 5'-CTTTCCTACA-3' (SEQ. ID. 6) | 10 |
| 12a | 5'-CCTACGTCTC-3' (SEQ. ID. 7) | 10 |
| 12b | 5'-CAACTAA-3' (SEQ. ID. 18) | 7 |
| 12c | 5'-CTTACGG-3' (SEQ. ID. 19) | 7 |
| 13 | 5'-CCCTC-3' (SEQ. ID. 20) | 5 |

| Strand | Domain Composition | Length (nt) |
|---|---|---|
| T1 | 1 2 | 26 |
| T2 | 3 4 | 26 |
| P1 | 2 3 | 36 |
| L1 | 4* 3* 2* 1* | 52 |
| F | 2c 3a | 18 |
| RL | 3a* 2c* 2b* | 25 |
| T3 | 5 6 7 8 | 36 |
| T4 | 9 10 ROX | 23 |
| P2 | 7 9 | 36 |
| L2 | RQ 10* 9* 7* 6* | 48 |

*The sequences of the starred complement domains are determined by the corresponding unstarred domains. For example, the 10 domain has sequence 5'-AACTC-3', so 10* has sequence 5'-GAGTT-3'. Strands are shown as concatenations of domains, listed from 5' to 3' end.

As described above, the conceptual design of the inventive system, such as the domain lengths and relative binding strengths, is based on the expected operational concentration and the desired binding fraction of individual targets in the absence of the second target. In particular, domains 1 and 4, described below, were designed so that, individually, their hybridization energies were insufficient to overcome the entropic loss of co-localizing one additional molecule of DNA, but collectively, they do drive the reaction forward. Although the examples are of designed molecules of DNA, it should be understood that in a system in which the target oligonucleotides are naturally occurring or otherwise non-designed, the lengths of domains 1 and 4 can still be selected so as to satisfy the prescribed conditions The lengths and sequences of the 2 and 3 domains were chosen so that spontaneous dissociation of P1 from state I or J would be extremely unlikely. For average 15-mers (with $\Delta G^0 \approx 21$ kcal/mol), the dissociation time is estimated to be roughly 10 years, which is far longer than the timescale of the reactions being monitored. However, in order to account for synthesis errors that could destabilize the binding of these domains to their complements, the lengths of the 2 and 3 domains were chosen to be 18 nt. It is expected that the devices would work similarly for domains 2 and 3 of equal or longer length, except insofar as the kinetics of branch migration would be slowed for long domains.

These considerations may be discussed in mathematical terms. Take, for example, the sequences of the 1 and 4 domains. There are two criteria on the lengths and sequences of the 1 and 4 domains, namely, the thermodynamics of 1 and 4 binding to their complement domains in D1 should overcome the configuration entropy loss of co-localizing another molecule (T1+T2+D1→P1+H1). Consider the equilibrium distribution of T1, T2, D1, P1, and H1:

$$K_{eq} = \frac{[P1][H1]}{[T1][T2][D1]} = e^{-\Delta G^0/RT} \qquad \text{EQ. 1}$$

$$\frac{[P1][H1]}{[T1][T2]} = e^{-\Delta G^0/RT + \ln([D1])} \qquad \text{EQ. 2}$$

$$\frac{[P1][H1]}{[T1][T2]} = e^{-\{\Delta G^0 - RT\ln([D1])\}/RT} \qquad \text{EQ. 3}$$

In the above, the reaction is driven to more than 50% completion when [P1][H1]/[T1][T2]>1, which is equivalent to saying $\Delta G^0 - RT \ln([D1]) < 0$. The value of $\Delta G^0$ for the reaction can be calculated as:

$\Delta G^0 = \Delta G^0(P1) + \Delta G^0(H1) - \Delta G^0(T1) - \Delta G^0(T2) - \Delta G^0(D1)$, $\Delta G^0 = \Delta G^0(H1) - \Delta G^0(D1)$, $\Delta G^0 = (\Delta G^0(1) + \Delta G^0(2) + \Delta G^0(3) + \Delta G^0(4) - 2\Delta G^0_{init}) - (\Delta G^0(2) + \Delta G^0(3) - \Delta G^0_{init})$, $\Delta G^0 = \Delta G^0(P1) + \Delta G^0(H1) - \Delta G^0(T1) - \Delta G^0(T2) - \Delta G^0(D1)$, $$\Delta G^0 = \Delta G^0(4) - \Delta G^0_{init} \qquad \text{EQ. 4}$$

where $\Delta G^0(1)$ denotes the hybridization energy of domain 1 to its complement 1, and $\Delta G_{init}$ denotes the entropy penalty of initiating a helix formation. (See, e.g., SantaLucia, J. & Hicks, D., Annu. Rev. Biophys. Biomol. Struct. 2004, 33, 415-440, the disclosure of which is incorporated herein by reference.) The standard free energies of T1, T2, and P1 in this example are 0, since they have been designed not to possess secondary structure. It will be understood that in naturally occurring targets, the $\Delta G$ of these domains need to be considered when designing the intermediary complex.

The concentration of D1 is typically higher than that of T1 and T2, and does not change significantly through the course of the reaction, so [D1] can be approximated as $[D1]_0$, the initial concentration of D1. Substituting the expansion of $\Delta G^0$ into the inequality $\Delta G^0 - RT \ln([D1]) < 0$, where:

$\Delta G^0(1) + \Delta G^0(4) - \Delta G^0_{init} - RT \ln([D1]) < 0$ $$\Delta G^0(1) + \Delta G^0(4) < \Delta G^0_{init} + RT \ln([D1]) \qquad \text{EQ. 5}$$

In this equation, $\Delta G^0_{init}$ is approximated to be −1.8 kcal/mol at 25° C. [1], and at [D1]=10 nM, −RT ln([D1])=−10.9 kcal/mol. Thus, $\Delta G^0(1) + \Delta G^0(4) < −12.7$ kcal/mol. Assuming $\Delta G^0(1) \approx \Delta G^0(4)$, $\Delta G^0(1) < −6.4$ kcal/mol. This value roughly corresponds to lower bound of approximately 5 nt for domains with roughly equal distribution of G/C and A/T bases.

Second, the thermodynamics of 1 and 4 binding to their complement domains in D1 should be weak enough so that if only one target is present, then that target is thermodynamically favored to be not bound to D1. Similar analysis to the above leads to the upper bounds: $\Delta G^0(1), \Delta G^0(4) \geq RT \ln(c) + \Delta G^0_{init} = −12.7$ kcal/mol, corresponding to roughly 10 nt for domains with roughly equal distribution of G/C and A/T bases. Consequently, it can be seen that a value roughly in the middle of these bounds should be chosen. In this case, the lengths of both the 1 and 4 domains were chosen to be 8 nt.

Standard Free Energy Calculation

The standard free energies of complexes are needed in order to calculate the standard free energy of reactions, which in turn can be used to generate equilibrium and rate constants. NUPACK was used to calculate the standard free energies of DNA complexes. (See, Dirks, et al., cited above.) NUPACK uses a number of different parameters in its calculations; the values used are detailed and justified below.

Temperature was set to 25° C., as that was the temperature at which the data was collected. Salt concentration was set to 0.05M Na$^+$ and 0.0115M Mg$^{2+}$. In actuality, the experimental concentration of Na$^+$ is 0.002M, but 0.05M Na$^+$ was the lowest NUPACK allowed. However, since Mg$^{2+}$ acts as the main counterion, it is likely that this difference does not significantly change the standard free energies. The "dangles" parameter was set to ALL, so that dangles energies are incorporated for all bases flanking duplexes, regardless of whether it is paired. This is necessary because, by default, NUPACK does not incorporate the thermodynamics of coaxial stacks (such as at the nick in I, J, and H1). The reason NUPACK does not by default include coaxial stacking thermodynamics is that they are still not well-understood: Pyshnyi et al. report that the energetics of coaxial stacking near a nick depends significantly on the nearest neighbors (bases one away from the nick). (See, Pyshnyi, D. V. & Ivanova, E. M., *Nucleosides, Nucleotides, Nucleic Acids* 2004, 23, 1057-1064, the disclosure of which is incorporated herein by reference.) Setting dangles=ALL allows partial compensation of the energetics at the nicks.

The standard free energies of complexes determine the standard free energies of reactions, which in turn can be used to calculate the equilibrium constant of the reaction via $\Delta G^0 = −RT \ln(Keq)$. For a reaction with different numbers of reactants and products, Keq is not unitless, and its value will depend on its unit. Thus, the $\Delta G^0$ of a reaction may depend on the units used for expressing Keq. For example, Keq=1M is identical to saying Keq=1000 mM, but the former yields $\Delta G^0 = 0$ kcal/mol, while the latter yields $\Delta G^0 = −4.1$ kcal/mol at 25° C.

NUPACK reports the $\Delta G^0$ values of complexes based on the equilibrium constant of the complex's formation, calculated in mole fraction. Because the concentration of all nucleic acid molecules is negligible compared to that of water ((1000 g/L)/(18 g/mol)=55 M), the molarity of the oligonucleotides is roughly 1/55th that of their mole fractions. To convert the NUPACK reported $\Delta G^0$ into one that yields Keq expressed in molar, a corrective $(n-1)RT \ln(55)$ term is added, where n denotes the number of strands the DNA molecule possesses (i.e., +2.38 kcal/mol for every strand in excess of 1).

Intermediates I and J represent the three-stranded complexes on which branch migration is possible (domain 2 for I and domain 3 for J). Consequently, I and J each correspond to 19 isoenergetic branch migration states (I0 through I18 and J0 through J18, respectively). Each of these states has a $\Delta G^0$ calculated by NUPACK to satisfy the equilibrium constant in one of the following reactions:

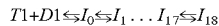

$$T1+D1 \leftrightharpoons I_0 \leftrightharpoons I_1 \ldots I_{17} \leftrightharpoons I_{18}$$

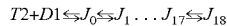

$$T2+D1 \leftrightharpoons J_0 \leftrightharpoons J_1 \ldots J_{17} \leftrightharpoons J_{18}$$

The standard free energies of the amalgamate states I and J are defined so as to preserve the equilibrium concentrations of D1 and T1 or T2. To do so, $-RT \ln(19) = -1.75$ kcal/mol is added to the $\Delta G^0$ of a single I0 or J0 state, respectively, to derive the $\Delta G^0$ of I or J. Table 2, below, shows the calculated free energies of the complexes.

TABLE 2

Figure 2:
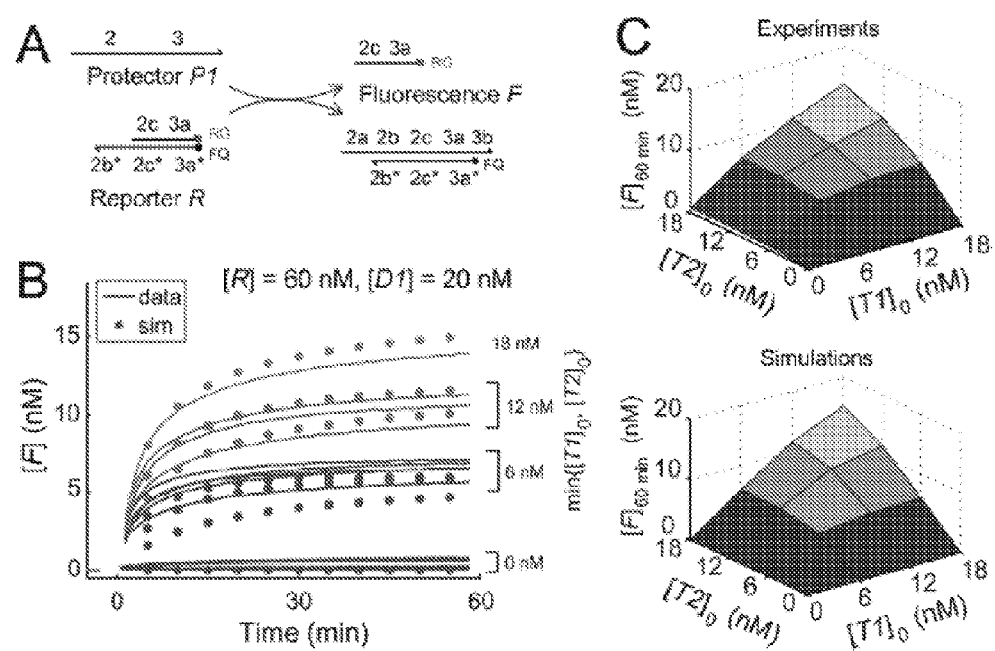
FIGS. 2A to 2C provide schematics (A), and data plots (B to C) summarizing studies characterizing and modeling cooperative hybridization reactions and individual rate constants, in accordance with an exemplary embodiment of the invention.

Composition and Standard Free Energies of Complexes Shown in FIGS. 1 and 2*

| Complex | Strand Composition | Calculated $\Delta G^0$ (kcal/mol) |
|---|---|---|
| D1 | P1, L1 | $-49.27 + 2.38 = -46.9$ |
| I | P1, L1, T1 | $-62.15 + 2(2.38) - 1.75 = -59.1$ |
| J | P1, L1, T2 | $-61.51 + 2(2.38) - 1.75 = -58.5$ |
| H1 | L1, T1, T2 | $-70.69 + 2(2.38) = -65.9$ |

*The standard free energies of these complexes were calculated using NUPACK, using the parameters 25° C., 0.05M Na$^+$, 0.0115M Mg$^{2+}$, dangles = ALL. The standard free energies of all individual strands were 0 kcal/mol (completely unstructured). Because NUPACK yields $\Delta G^0$ values that were calculated for mole fraction rather than molar, a corrective $RT\ln([H_2 0]) = +2.38$ kcal/mol term must be added for every strand in excess of 1. The intermediate states I and J each correspond to 19 isoenergetic branch migration states; the $-RT\ln(19) = -1.75$ kcal/mol term corrects for this state multiplicity.

Annealing

All annealing processes were performed with an Eppendorf Mastercycler Gradient thermocycler. The samples were brought down from 95 to 20° C. at a constant rate over the course of 75 min.

Complex Purification.

DNA oligonucleotides used in this study were purchased from Integrated DNA Technologies (IDT). Where applicable, fluorophores were attached by IDT as well. Concentrations were determined from the measured absorbance at 260 nm using an Eppendorf Biophotometer and calculated extinction coefficients. (See, e.g., Puglisi, J. D. & Tinoco, I., *Methods Enzymol.* 1989, 180, 304-325; and Owczarzy, R., et al., *Biochemistry* 2008, 47, 5336-5353, the disclosures of each of which are incorporated herein by reference.)

Complex D1 used in FIG. 2, described below, was purified by non-denaturing (ND) polyacrylamide gel electrophoresis (PAGE) to ensure proper stoichiometry as follows: The P1 and L1 strands were prepared with nominally correct stoichiometry at 20 μM and annealed. The samples were then run on 12% ND PAGE at 180 V for 6 h.

The acrylamide (19:1 acrylamide:bis) was diluted from 40% acrylamide stock (Ambion). ND loading dye containing xylene cyanol FF in 50% glycerol was added to all samples, achieving a final glycerol concentration of 10% by volume. Gels were run at 25° C. using a Novex chamber with an external temperature bath.

The proper D1 band was cut out and eluted in 2 mL of TE/Mg$^{2+}$ buffer for 2 days. Purified complexes were quantitated by 260 nm absorbance measurement and calculated extinction coefficients. Yield was approximately 50%. Notably, only the complex D1 used for experiments in FIG. 2 was purified; the D2 used in FIG. 3 and the D1 used in FIGS. 4 to 6 were not purified.

Buffer Conditions

DNA oligonucleotides were stored in TE buffer (10 mM Tris·HCl pH-balanced to 8.0, with 1 mM EDTA·Na2, purchased as 100× stock from Sigma-Aldrich) at 4° C. Directly preceding experiments, TE buffer with 62.5 mM MgCl$_2$ was added at a 1:4 ratio to the sample, achieving a final MgCl$_2$ concentration of 12.5 mM (of which 1 mM is bound to EDTA). This buffer is henceforth known as "TE/Mg$^{2+}$" buffer. All experiments and purifications were performed at 25±0.5° C., with temperature controlled using an external temperature bath.

Spectrofluorimetry Studies

Figure 2D:
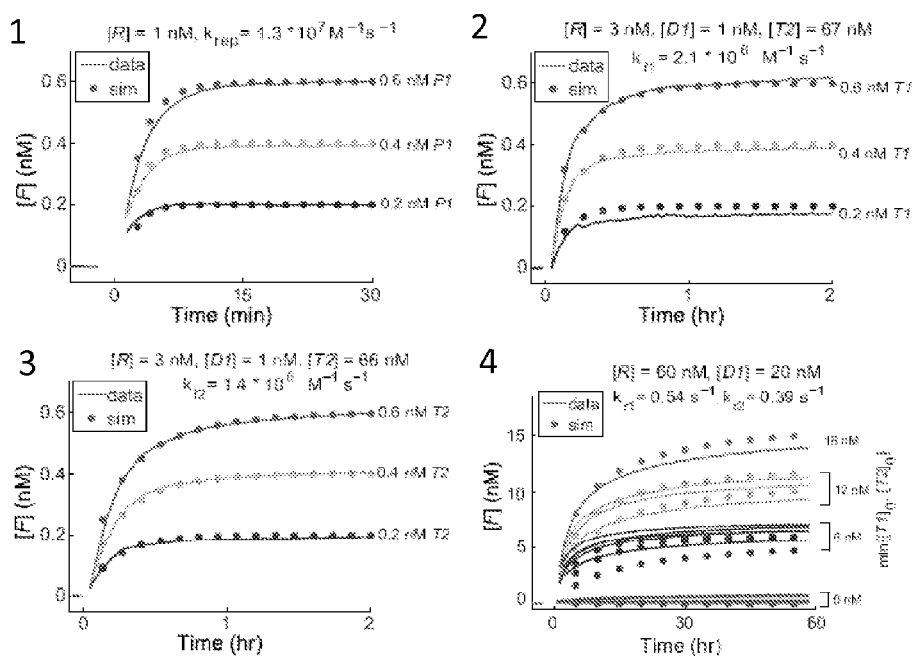

Spectrofluorimetry studies were done using a SPEX Fluorolog-3 (Horiba) with 1.6 mL 119-004F synthetic quartz cells (Hellma). For the experiments shown in FIGS. 3, 5D, and 6, excitations were at 588 nm, while emissions were at 602 nm (optimal signal for ROX fluorophore). For the experiments shown in FIGS. 2, 4, and 5B, excitations were at 510 nm, while emissions were at 531 nm (optimal signal for Rhodamine Green fluorophore). In all spectrofluorimetry experiments, the total reaction volume was 1.5 mL. For FIGS. 2D$_{1-3}$, 3B & C, 5E, and 6, 4 nm band-pass slits were used for both excitation and emission monochromators. For all other experiments, 2 nm slits were used. In all experiments, data points were collected with an integration time of 10 s for every 60 s time point.

Prior to each experiment, all cuvettes were cleaned thoroughly: each cuvette was washed 15 times in distilled water, once in 70% ethanol, another five times in distilled water, and finally once more in 70% ethanol. For the slit size, concentrations, and times chosen, no measurable photobleaching was observed. All experimental results were within the linear regime of the spectrofluorimeter detector, according to the specification sheets provided by the manufacturer.

Fluorescence Normalization

Figure 3:
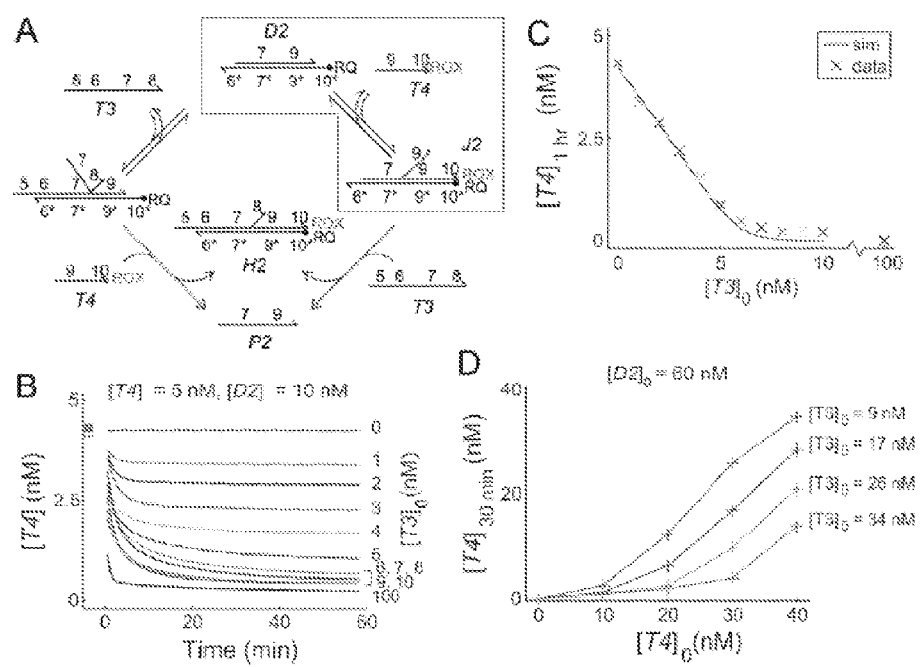
Figure 4:
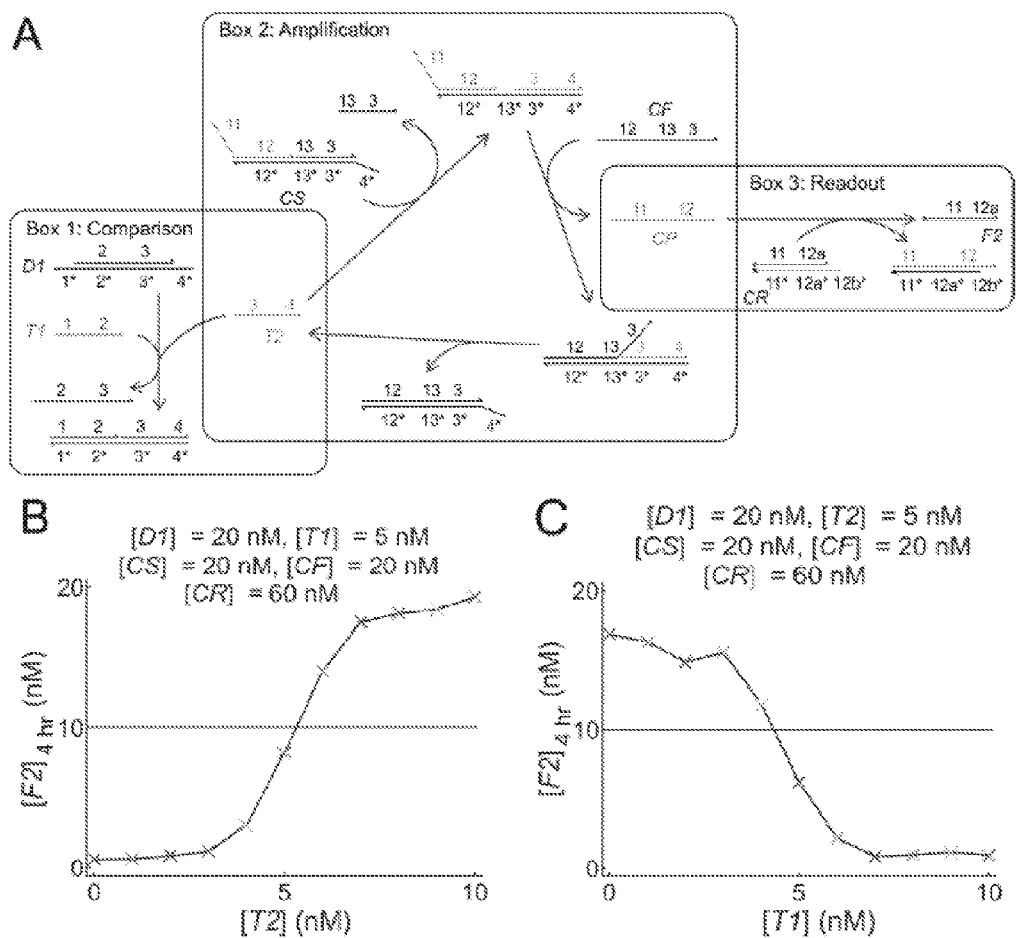
Figure 4:
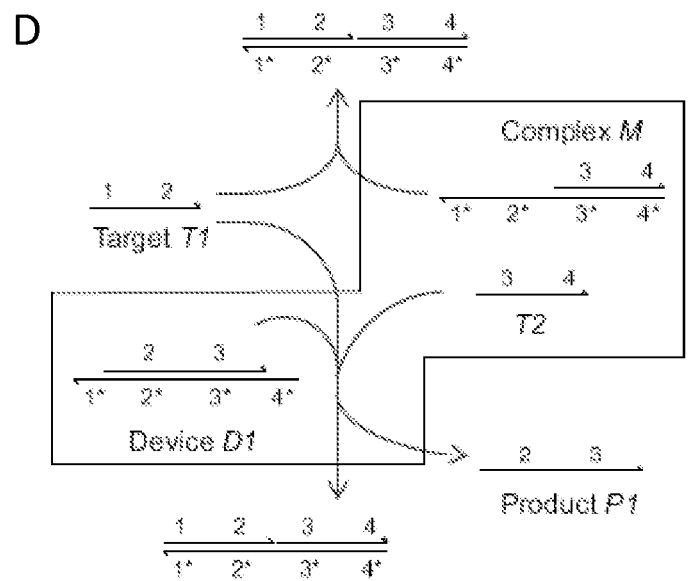
Figure 4:
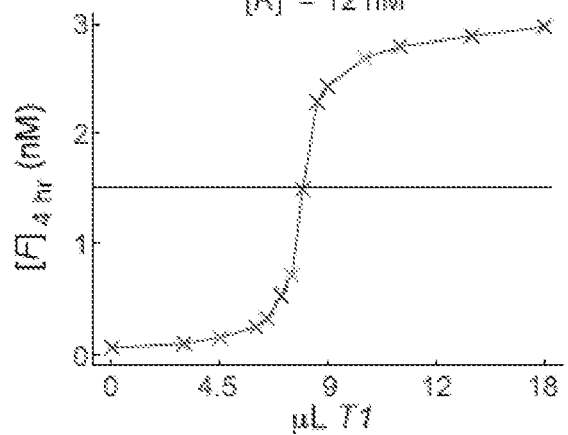
Figure 5:
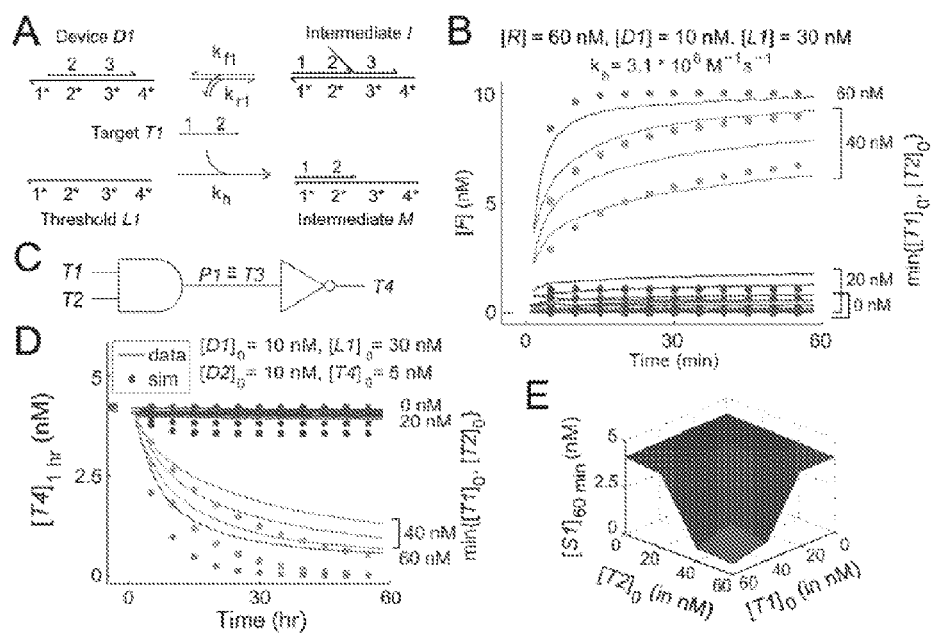

Fluorescence is normalized so that 1 normalized unit (n.u.) of fluorescence corresponds to 1 nM of an unquenched fluorophore-labeled strand (F in FIGS. 2 and 5B, T4 in FIGS. 3, 5D, and 6, and F2 in FIG. 4). This normalization is based on the fluorescence levels of annealed samples: a negative control with [R]=30 nM yielded the fluorescence of the quenched F strand (Rhodamine Green), and a positive control with [R]=30 nM and [P1]=10 nM yielded the fluorescence of the unquenched F strand. Similarly, a negative control with [T4]=5 nM and [L2]=10 nM yielded the fluorescence of the quenched T4 strand (ROX), and a positive control with [T4]=5 nM yielded the fluorescence of the unquenched T4 strand. Day-to-day and sample-to-sample variations in fluorescence are estimated to be less than 5%.

Ordinary Differential Equation (ODE) Simulations

Reaction simulations were run in Matlab using the "stiff" ode23s solver because of the difference in time scales of bimolecular and unimolecular reactions. The relative tolerance of the solver was set to $10^{-4}$, and the absolute tolerance of the solver was set to $10^{-30}$ M.

Parameter Fitting

Rate constants were fitted to experimental data using the "fminunc" function in Matlab to minimize the error between experimental data and the reaction model. The error between the data and the simulation is calculated as:

$$\text{Error} = \sum_{t, traces} (F_d(t) - F_m(t))^2 \qquad \text{EQ. 6}$$

where $F_d(t)$ is the fluorescence value of the data at time t, and Fm(t) is the fluorescence value predicted by the ODE model at time t. The confidence intervals on the values of the rate constants were generated as the values of the rate constant at which the error score is double that of the minimum. All other rate constants were kept constant at their best-fit values when generating the confidence interval on each rate constant.

EXAMPLE 1

Characterizing Cooperative Hybridization

To demonstrate that the cooperative hybridization mechanism functions as intended, two different properties must be independently verified: first that T1 and T2 when simultaneously present can cooperatively hybridize to D1, and second that T1 in the absence of T2 or T2 in the absence of T1 is insufficient to stably bind D1.

FIG. 2 shows the kinetic behavior of the cooperative hybridization system through the use of a fluorescent reporter complex R that reacts stoichiometrically with P1. In particular, FIG. 2A shows a schematic of the reaction pathway of a cooperative hybridization reaction assayed through the use of a fluorescence reporter complex R (comprised of F and RL), in this reaction P1 reacts stoichiometrically with R to release fluorophore-labeled strand F, where RG denotes Rhodamine Green, and FQ denotes the Iowa Black Fluorescence Quencher. The release of P1 and the subsequent fluorescence increase is seen to vary linearly with the minimum of the initial concentrations of T1 and T2, supporting the proposed mechanism.

FIG. 2B shows the kinetics of the cooperative hybridization reaction. In this example, R and D1 were present in solution initially, and various quantities of T1 and T2 were introduced at time t≈0. Because D1 is in excess of both T1 and T2, both the kinetics and the final equilibrium fluorescence value depend on the minimum of the concentrations of T1 and T2.

Also shown in FIGS. 2B & C are simulation results (dotted lines), using individually measured rate constants, with fluorescence plotted against the concentrations of T1 and T2. These figures show that the release of P1 (and subsequently F) is contingent upon the simultaneous presence of T1 and T2. The reactions simulated and their relevant rate constants are summarized in Table 3, below.

TABLE 3

Reaction Kinetics and Thermodynamics

Reaction and Rate Constants Simulated in FIGS. 2B & C[a]

| Reactions | Rate Constants[b] |
|---|---|
| T1 + D1 $\underset{k_{r1}}{\overset{K_{f1}}{\rightleftharpoons}}$ I | $k_{f1} = (2.1 \pm 0.7) \times 10^6 M^{-1}s^{-1}$ |
| T2 + D1 $\underset{k_{r2}}{\overset{K_{f2}}{\rightleftharpoons}}$ J | $k_{f2} = (1.4 \pm 0.2) \times 10^6 M^{-1}s^{-1}$ |
| T2 + I $\overset{K_{f2}}{\longrightarrow}$ P1 + H1 | $k_{r1} = 0.54 \pm 0.42\ s^{-1}$ |

TABLE 3-continued

Reaction Kinetics and Thermodynamics

| Reactions | Rate Constants |
|---|---|
| T1 + J $\overset{K_{f1}}{\longrightarrow}$ P1 + H1 | $k_{r2} = 0.39 \pm 0.27\ s^{-1}$ |
| P1 + R $\overset{K_{rep}}{\longrightarrow}$ F + Fw | $k_{rep} = (1.3 \pm 0.5) \times 10^7 M^{-1}s^{-1}$ |

Standard Free Energies of Reactions Simulated in FIGS. 2B & C[c]

| Reaction | Calculated ΔG⁰ (kcal/mol) | Fitted ΔG⁰ (kcal/mol) |
|---|---|---|
| T1 + D1 $\underset{k_{r1}}{\overset{K_{f1}}{\rightleftharpoons}}$ I | −12.2 | −9.00 |
| T2 + D1 $\underset{k_{r2}}{\overset{K_{f2}}{\rightleftharpoons}}$ J | −11.6 | −8.95 |
| T2 + I $\overset{K_{f2}}{\longrightarrow}$ P1 + H1 | −6.8 | N/A |
| T1 + J $\overset{K_{f1}}{\longrightarrow}$ P1 + H1 | −7.4 | N/A |

[a]The simulations use the best-fit value of the rate constants; the errors bars on the rate constants are calculated as described in Materials and Methods, Parameter Fitting
[b]The individual rate constants of various intermediate reactions are characterized as follows. The $k_{rep}$ rate constant for the P1 + R → F + Fω reporter reaction is measured in FIG. 2D₁. This rate constant is significantly higher than those of similar reporter complexes, though the reason for this is not understood.
The rate constants of strand displacement reactions involving fluorophore and quencher-labeled DNA oligonucleotides generally cannot be predicted as reliably as those of unfunctionalized DNA. The $k_{f1}$ and $k_{f2}$ rate constants are also measured in FIGS. 2D₂₋₄.
These values are consistent with previous characterizations of strand displacement rate constants, which ranged from $3 \cdot 10^5\ M^{-1}s^{-1}$ to $6 \cdot 10^6\ M^{-1}s^{-1}$ for 8 nt toeholds, depending on the sequence of the toehold.
(See, Zhang, D. Y., et al., Science 2007, 318, 1121-1125; Zhang, D. Y. & Winfree, E., J. Am. Chem. Soc. 2009, 131, 17303-17314; and Marras, S. A. E., et al., Nuc. Acids Res. 2002, 30, e122, the disclosures of each of which are incorporated herein by reference.)
[c]Calculated ΔG⁰ (25° C.) denotes the value obtained from using the NUPACK predicted standard free energies of the complexes, and the fitted ΔG⁰ denotes the value obtained from ΔG⁰ = −RTln(kf/kr).
The fitted ΔG⁰ of the latter two reactions cannot be calculated because the reverse reaction was too slow to observe: according to the calculated ΔG⁰, the reverse rate constant would be around $10\ M^{-1}s^{-1}$, corresponding to a time scale of about 3 months at an operational concentration of 10 nM.

The agreement between ODE simulations and experimental data further supports that the cooperative hybridization mechanism functions as designed: the consumption of T1, the consumption of T2, and the production of P1 are all simultaneous and stoichiometric with respect to each other. The small quantitative differences between simulations and experiments are likely due to oligonucleotide impurities, as discussed above, and undocumented side reactions (such as T2+R→F).

FIG. 3 demonstrates that the two DNA oligonucleotide targets do not unilaterally bind irreversibly to the two-stranded complex. Here, as shown in the schematic of FIG. 3A, different sequences are used, with T3 and T4 cooperatively hybridizing to complex D2. T4 is labeled with the ROX fluorophore, and the bottom strand L2 of the D2 complex is quencher-labeled with the Iowa Black Red Quencher. Thus, when T4 is hybridized to D2, either temporarily or permanently, the fluorophore is co-localized to the quencher and the observed fluorescence is decreased. In the absence of T3, however, T4 should not significantly bind to D2. This allows a direct assay of the instantaneous concentration of free T4. The other oligonucleotide target T3 possesses both 5' and 3' overhangs that serve no function for the cooperative hybridization mechanism. The existence of these overhangs demonstrates that the cooperative hybridization mechanism can be used to target a subsequence of a longer nucleic acid, such as an mRNA.

FIG. 3B shows the results of this system, and that support the mechanism set forth in the invention. In the system, D2 and T4 are initially present, and fluorescence is similar to that of T4 alone. As various amounts of T3 are introduced into the reaction at t≈0, the fluorescence decreases. In particular, the fluorescence of solution in the absence of T3 is between 4 and 4.5 nM, while $[T4]_0=5$ nM. A small fraction of the T4 is associated to D2 at equilibrium. When an amount of T3 is added to the system, the fluorescence (concentration of free T4) re-equilibrates, consistent with the cooperative hybridization mechanism of the current invention.

The stoichiometric consumption of the two single-stranded reactants in cooperative hybridization can be interpreted as analog subtraction. If initially $[T4]_0>[T3]_0$, then the equilibrium concentration of free T4 will be $[T4]_\infty \approx [T4]_0-[T3]_0$. This property can be used to compare the concentrations of oligonucleotides of known sequences. For example, T4 can act as a well-characterized standard, and a different D2 complex can be constructed for each nucleic acid molecule T3 of interest. In a solution of a known quantity of T4 and an excess of D2, the concentration of T3 can be inferred from the equilibrium fluorescence (see Example 2, below). Because the same standard T4 can be used to quantitate a variety of different oligonucleotides, quantitation using cooperative hybridization may yield advantages over methods based on molecular beacons because of the reduced need for calibration. (See, Tyagi, S. & Kramer, F. R., *Nat. Biotechnol.* 1996, 14, 303-308, the disclosure of which is incorporated herein by reference.)

From the data shown in FIG. 3B, the concentrations of T3 and T4 are implied to differ from their nominal values calculated from absorbance at 260 nm. Arbitrarily assuming that the concentration of T4 is accurate, the true concentration of T3 is inferred to be 14% lower than given. This 14% difference may arise due to errors in extinction coefficients, sample impurities that yield absorbance at 260 nm, and/or truncated oligonucleotides that cannot undergo cooperative hybridization. FIG. 3C shows simulation results assuming that the concentrations of T3 are 14% lower than listed, and FIG. 3D shows the equilibrium concentrations of T4 based on a variety of initial concentrations of T3 and T4 (with the corrected concentration of T3).

Table 4, below, shows the reactions simulated to generate the simulation traces shown in FIG. 3C. Five different parameters were fitted to the data in FIG. 3C (the four rate constants and the concentration of T3). As shown, fluorescence after 1 h follows a kinked line, with the kink roughly at [T3]=5 nM. As is discussed in greater detail in Example 2, below, the cooperative hybridization mechanism can be used as a method of quantitating nucleic acid concentrations given a known standard of independent sequence. Simulation traces shows the predicted results according to the current model, fitting the T3 concentration to be 14% lower than as measured by absorbance. Given the limited data on this system, the fit was underconstrained, and it is likely that many different sets of rate constant values would have yielded fits of similar quality. The length of domain 6 is 7 nt, rather than 8 nt as in domains 1 and 4, because of the thermodynamically stabilizing effect of the 5' dangle. (See, SantaLucia, J. & Hicks, D., *Annu. Rev. Biochem.* 2004, 33, 415-440, the disclosure of which is incorporated herein by reference.) The length of domain 10 is 5 nt, rather than 7 or 8, because of the stabilizing effects of fluorophore-quencher binding on the thermodynamics of DNA hybridization. (See, Marras, S. A. E., et al., *Nucleic Acids Res.* 2002, 30, e122, the disclosure of which is incorporated herein by reference.) These experiments suggest that the interaction between ROX and Iowa Black Red Quencher is similar to that of 4-5 base pairs binding (data not shown).

TABLE 4

Reactions Simulated in FIGS. 3B & C*

| Reactions | Rate Constants |
|---|---|
| T3 + D2 $\underset{k_{r3}}{\overset{K_{f3}}{\rightleftharpoons}}$ I2 | $k_{f3} = 4 \times 10^6$ M$^{-1}$s$^{-1}$ |
| T4 + D2 $\underset{k_{r4}}{\overset{K_{f4}}{\rightleftharpoons}}$ J2 | $k_{f4} = 4 \times 10^6$ M$^{-1}$s$^{-1}$ |
| T4 + I2 $\xrightarrow{K_{f4}}$ P2 + H2 | $K_{r3} = 0.3$ s$^{-1}$ |
| T3 + J2 $\xrightarrow{K_{f4}}$ P2 + H2 | $K_{r4} = 0.2$ s$^{-1}$ |

*The data displayed in FIG. 3 under constraint the rate constants. Shown here are one set of rate constant values that generated reasonably good agreement between ODE simulations and experimental data. Similar qualities of fit can be attained by co-varying the four rate constants.

Finally, in FIG. 3D, the equilibrium concentration of free T4 (which is roughly linear to fluorescence) is the difference between the initial concentrations of T4 and T3. The data displayed shows the fluorescence after 30 min, as a function of T3 and T4 concentration. Fluorescence appears to be roughly linear in the concentration excess of T4 over T3. This figure shows that the individual binding of T3 or T4 to D2 is reversible and not favorable at equilibrium, and that the hybridization mechanism of the instant invention is cooperative as designed.

EXAMPLE 2

Concentration Quantitation

The cooperative and simultaneous nature of the hybridization of two target oligonucleotides to the two-stranded complex means that the cooperative hybridization mechanism can easily be applied to quantitating nucleic acids. For example, in FIG. 2, consider T4 as a standard of known concentration, against which we measure the concentration/quantity of a sample with an unknown amount of target oligonucleotide T3. With increased amounts of T3 in the sample solution, the equilibrium fluorescence of the mixture of T3 and T4 decreases, until the minimum where the quantity of T3 exceeds that of T4. Thus, one can use cooperative hybridization to accurately determine the concentration of a nucleic acid species, relative to that of a standard oligonucleotide of independent sequence.

In particular, the equilibrium fluorescence of the mixture of T3 and T4 initially decreases linearly with the concentration of T3; thus linear response facilitates the quantitation process. To mathematically show that the fluorescence is linear in the quantity of T3, we first consider the components of the observed fluorescence. There are three sources of fluorescence signal in the experiments described in FIG. 2: the unquenched fluorophores in T4, the quenched fluorophores in J2 and H2, and the background fluorescence. Define b to be the background fluorescence. Define a to be the fluorescence per unit of the unquenched fluorophore. Define q to be the quenching ratio of the fluorophore (the fluorescence of the unquenched fluorophore divided by the fluorescence of the quenched fluorophore). Thus, the fluorescence f of a solution can be written as:

$$f = a[T4] + \frac{a}{q}([J2] + [H2]) + b, \quad \text{EQ. 7}$$

$$= \frac{a(q-1)}{q}[T4] + \frac{a[T4]_{tot}}{q} + b$$

where $[T4]_{tot}=[T4]+[J2]+[H2]$ is the total concentration of T4 in solution. As can be seen, the fluorescence f is linear in [T4].

In the idealized case when the sample solution containing the target reaches equilibrium with the test solution containing the standard and device, and where the fluorescence readout is infinitely accurate, the concentration of the target in the sample solution can be easily calculated from a single experiment. Define x to be the volume of sample solution that reacted with y volume of test solution. The system operates under the assumption that y≥x. Define the concentration of T3 in the sample solution to have been $[T3]_s$. Define the total concentrations of T4 and D2 (including the portion sequestered in L2) in the test solution to have been $[T4]_t$ and $[D2]_t$, respectively. Thus, there are $x[T3]_s$ moles of T3, $y[T4]_t$ moles of T4, and $y[D2]_t$ moles of D2. In order for quantitation to be possible, $y[T4]_t > x[T3]_s$ (i.e. standard exceeds target).

Define $[T4]_m$, $[D2]_m$, and $[J2]_m$ to be the concentrations of free T4, free D2, and intermediate J2 in the mixture of the sample and test solutions at equilibrium. $[T4]_m$ is inferred from the fluorescence level, and $[T3]_s$, the concentration of the target in the initial sample solution, is to be derived.

$$\frac{y[T4]_t - x[T3]_s}{x+y} = [T4]_m + [J2]_m \quad \text{EQ. 8}$$

$$\frac{y[D2]_t - x[T3]_s}{x+y} = [D2]_m + [J2]_m$$

Reorganizing, $$[J2]_m = \frac{y[T4]_t - x[T3]_s}{x+y} - [T4]_m \quad \text{EQ. 9}$$

$$[D2]_m = [T4]_m + \frac{y([D2]_t - [T4]_t)}{x+y}$$

From the equilibrium of the mixture the following are obtained:

$$K_{eq} = \frac{[J2]_m}{[T4]_m[D2]_m} \quad \text{EQ. 10}$$

$$= \frac{\frac{y[T4]_t - x[T3]_s}{x+y} - [T4]_m}{[T4]_m\left([T4]_m + \frac{y([D2]_t - [T4]_t)}{x+y}\right)}$$

$$K_{eq}[T4]_m\left([T4]_m + \frac{y([D2]_t - [T4]_t)}{x+y}\right) + [T4]_m = \frac{y[T4]_t - x[T3]_s}{x+y} \quad \text{EQ. 11}$$

$$[T3]_s = \frac{y[T4]_t}{x} - \quad \text{EQ. 12}$$

$$\frac{K_{eq}y([D2]_t - [T4]_t) + x + y}{x+y}[T4]_m - \frac{K_{eq}(x+y)}{x}[T4]_m^2$$

Every variable on the right hand side of the equation is known (with $K_{eq}$ calculated from the $\Delta G^0$ of the reaction); thus, $[T3]_s$ can be calculated from observed fluorescence.

Given that at experimental concentrations, the reactions could take quite long to reach equilibrium, it is possible instead to use a series of experiments with various different volumes of the sample solution reacting with the test solution. This is the method used to quantitate the concentration of T3 shown in FIGS. 2B & C. As the volume of the sample solution increases, the amount of T3 eventually overtakes that of the standard T4. The volume of sample solution at which the amount of T3 stoichiometrically matches that of T4 is here denoted as the matching volume.

When the matching volume of the sample solution is added to the test solution, then at equilibrium all of the T4 will be sequestered in waste H2 and quenched. Further addition of sample solution will only slightly decrease the fluorescence (due to dilution of the quenched fluorophore in H2). It takes a long time for equilibrium to be established when the exact matching volume of the sample solution is added due to the second-order nature of the J2+T3→P2+H2 reaction, but equilibrium is more quickly approached when the amount of sample solution added deviates significantly from the matching volume (the reaction kinetics become pseudo-first order due to the excess of either J2 or T3).

Figure 2E:
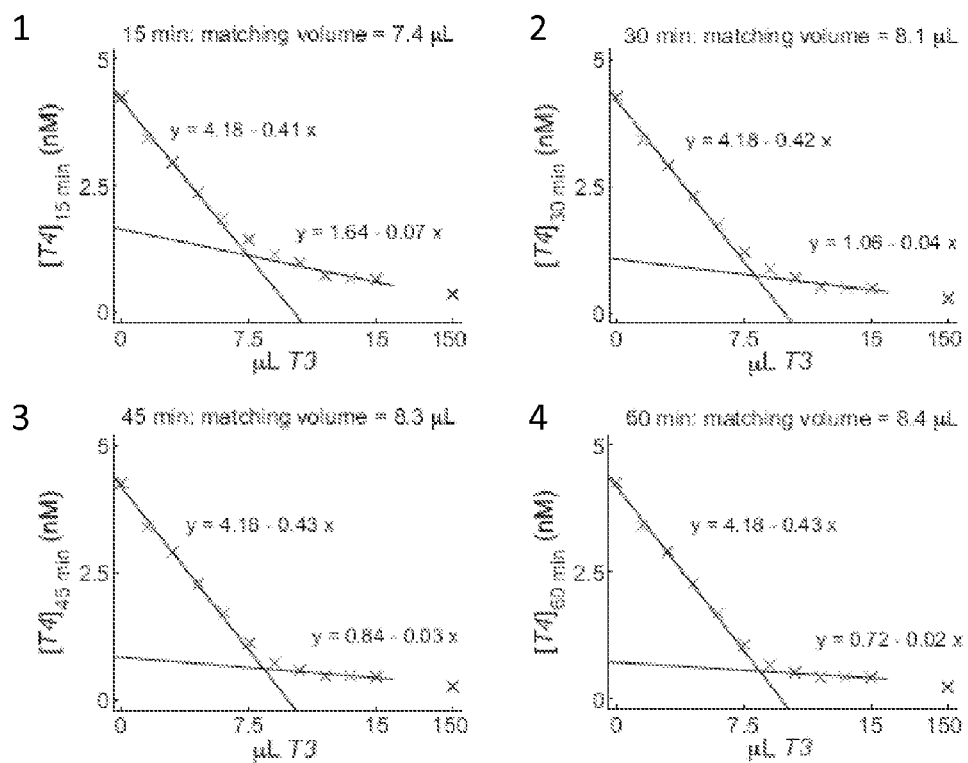

Given the fluorescence of various mixtures with different amounts of sample solution at a particular time point, the matching volume can be estimated by the intersection of two linear fits of fluorescence to sample solution volume (FIG. $2E_{1-4}$). The data from the later time points are expected to be more reliable because the reaction has proceeded closer to equilibrium, and because the earlier data points may be affected more strongly by incomplete mixing and experimental error on the reported time points. The linear fits in FIG. 2E use 4 data points each; Table 5 shows the inferred matching volumes based on linear fits using 3, 4, and 5 data points. As can be seen, the inferred matching volumes are quite similar regardless of how many data points are used in the linear fits.

From the data shown, the matching volume is seen to be 8.4±1.0 µL. Assuming that the concentration of the standard T4 is accurate at 5 nM, the total amount of T4 is 5 nM·1.5 mL=7.5 pmol, and the inferred concentration of T3 in the sample solution is $$\frac{7.5 \text{ pmol}}{8.4 \pm 1.0 \mu L} = 0.89 \pm 0.12 \ \mu\text{M},$$

or 0.9±0.1 µM after accounting for significant digits.

TABLE 5

| | Inferred Matching Volume of T3 | | |
|---|---|---|---|
| Time (min) | 3 points (µL) | 4 points (µL) | 5 points (µL) |
| 15 | 7.8 | 7.4 | 7.5 |
| 30 | 8.1 | 8.1 | 8.1 |
| 45 | 8.3 | 8.3 | 8.3 |
| 60 | 8.3 | 8.4 | 8.4 |

We wish to show that the fluorescence ($[T4]_m$) decreases pseudo-linearly with the amount of T3 added ($x[T3]_s$). Rearranging EQ. (11) is:

$$K_{eq}(x+y)[T4]_m^2 + (K_{eq}y([D2]_t-[T4]_t)+x+y)[T4]_m-x[T3]_s)=0 \quad \text{EQ. 13}$$

Solving this quadratic relation yields EQ. 14, below:

$$[T4]_m = -\frac{K_{eq}y([D2]_t - [T4]_t) + x + y}{2K_{eq}(x+y)} +$$

$$\frac{\sqrt{(K_{eq}y([D2]_t - [T4]_t) + x + y)^2 + 4K_{eq}(x+y)(y[T4]_t - x[T3]_s)}}{2K_{eq}(x+y)}$$

The second term can be approximated as $$\frac{1}{2K_{eq}(x+y)}(x + y + K_{eq}y([D2]_t - [T4]_t) + 2K_{eq}(y[T4]_t - x[T3]_s)) \quad \text{EQ. 15}$$

if $2K_{eq}(y[T4]_t - x[T3]_s)$ is small compared to $x+y+K_{eq}y([D2]_t-[T4]_t)$. It will be shown that this is the case shortly. For now, the approximation can be used, substituting back into the expression for $[T4]_m$:

$$[T4]_m \approx -\frac{K_{eq}y([D2]_t - [T4]_t) + x + y}{2K_{eq}(x+y)} +$$

$$\frac{x + y + K_{eq}y([D2]_t - [T4]_t) + 2K_{eq}(y[T4]_t - x[T3]_s)}{2K_{eq}(x+y)}$$

$$= \frac{2K_{eq}(y[T4]_t - x[T3]_s)}{2K_{eq}(x+y)}$$

$$= \frac{y[T4]_t}{x+y} - \frac{1}{x+y}x[T3]_s$$

The final relationship between $[T4]_m$ and $x[T3]_s$ is thus seen to be approximately linear. This pseudo-linearity depends upon the condition:

$$2K_{eq}(y[T4]_t - x[T3]_s) \ll x+y+K_{eq}y([D2]_t-[T4]_t) \quad \text{EQ. 17}$$

It is possible to solve for the conditions under which:

$$2K_{eq}(y[T4]_t - x[T3]_s) < 0.5(x+y+K_{eq}y([D2]_t-[T4]_t)) \quad \text{EQ. 18}$$

When this is true, the difference between the approximate $[T4]_m$ and the real $[T4]_m$ is less than 20%. Rearranging this relation gives:

$$4K_{eq}(y[T4]_t - x[T3]_s) \ll x+y+K_{eq}y([D2]_t-[T4]_t) \quad \text{EQ. 19}$$

The left hand side is smaller than $4K_{eq}y[T4]_t$, and the right hand side is greater than y, so a sufficient condition is:

$$4K_{eq}y[T4]_t < y \quad \text{EQ. 20}$$

$$K_{eq} < \frac{1}{4[T4]_t}$$

Recall that $$K_{eq} = \frac{[J2]}{[T4][D2]},$$

so:

$$\frac{[J2]}{[T4][D2]} < \frac{1}{4[T4]_t} \quad \text{EQ. 21}$$

$$\frac{[J2]}{[T4]} < \frac{[D2]}{4[T4]_t}$$

When $[D2] \geq 2[T4]_t$, $[D2]$ is necessarily greater than $[T4]_t$, so the right hand side is greater than ¼. Thus, the necessary condition for the approximation is satisfied whenever $$\frac{[J2]}{[T4]} < \frac{1}{4}.$$

This equates to saying that operational concentrations must be low enough that the T4+D2 J2 reaction favors the reactants by at least a 4:1 ratio.

EXAMPLE 3

Reaction Networks Involving Cooperative Hybridization

Cooperative hybridization is a modular dynamic DNA nanotechnology component that can be integrated with other systems to form reaction networks with desired properties. In FIG. 4, cooperative hybridization is cascaded with a DNA hybridization based catalyst system and a fluorescent reporter to yield a network that performs digital concentration comparison of two different oligonucleotides. (See, Zhang, D. Y., et al., Science 2007, 318, 1121-1125, the disclosure of which is enclosed by reference.) This could potentially be used for detecting over-expression and under-expression of nucleic acids relative to certain thresholds.

In this reaction network, T2 serves as the catalyst for releasing CP from multistranded complex CS. Because T2 cooperatively hybridizes to D1 with T1, if the concentration of T1 exceeds that of T2, then little to no free T2 will exist, and CP will not be released. In contrast, if [T2] exceeds [T1], even if only by a little, then it catalytically releases CP, and the final fluorescence value will be determined by the concentration of precursor CS initially present in solution. Thus, the thresholded linear response shown in FIG. 3C is converted to the sigmoidal thresholded response shown in FIGS. 4B & C. Alternative methods of digitally comparing nucleic acid concentrations using cooperative hybridization also exist.

For example, an alternative mechanism for implementing only sigmoidal thresholding is shown in FIG. 4D. In this case, it is possible to make use of complex M, which is formed by combining an equal amount of T2 and L1. Subsequently, a small amount of P1 is added, and displaces T2, forming an equal amount of D1 and T2. Next, the sample with an unknown amount of T1 is added. T1 preferentially reacts with M because there are more toehold bases to initiate hybridization, and because the reaction is irreversible. Only when M is exhausted does T1 start to significantly react with D1. At this point, the T1 and T2 cooperatively hybridize to D1, releasing P1, which results in a fluorescence increase. FIG. 4E shows the fluorescence value 4 hours after the sample containing T1 is added. From this figure, the concentration of T1 is inferred to be 13% higher than that calculated from absorbance at 260 nm, assuming that the concentration of M is accurate. In particular, the sigmoidal response curve allows precise quantitation. As shown, the fluorescence crosses the half-max threshold at 8.0±0.2 μL, T1, implying T1 concentration to be $$\frac{1.5 \text{ mL} \cdot 60 \text{ nM}}{8.0 \pm 0.2 \text{ μL}} = 11.3 \pm 0.3 \text{ μM}.$$

In addition to providing a sigmoidal thresholded response, this reaction network also amplifies the fluorescence signal relative to the concentrations of the targets. In FIGS. 4B & C, the concentrations of T1 and T2 were both less than 10 nM, yet the final fluorescence corresponded to up to 20 nM of released fluorophore-labeled strands, demonstrating thresholded amplification using purely DNA components. Further amplification can be achieved through multilayer catalyst cascades or feedback systems. (See, Soloveichik, D., et al., *Proc. Natl. Acad. Sci. U.S.A.* 2010, 107, 5393-5398, the disclosure of which is incorporated herein by reference.)

Although the above discussion has focused on the case where different target oligonucleotides are used, the system and method may also include the case where the two target oligonucleotides are identical in sequence, such that there exists only one unique target oligonucleotide. In such an embodiment the release of product and the production of the dual-hybridized product will both follow a sigmoidal relation with the concentration of the target.

EXAMPLE 4

Logical Processing Using Cooperative Hybridization

The properties of cooperative hybridization can be interpreted as implementations of Boolean logic. For example, in FIG. 1, P1 can be considered the output of a logical AND gate, with T1 and T2 being the inputs. Alternatively, in FIG. 3, T4 can be considered the output of a logical NOT gate, with T3 being the input.

One key feature of Boolean logic is digital abstraction, wherein analog values are converted to digital ones through sigmoidal thresholding and amplification, both of which have been demonstrated in FIG. 4. However, a simpler method of thresholding can be achieved using excess L1, the bottom strand of D1 (FIG. 5A). Targets T1 and T2 preferentially bind L1 over D1 because L1 offers a longer single-stranded toehold for initiating hybridization and because individual hybridization is irreversible. FIG. 5B shows that when either [T1] or [T2] is less than [L1], little product P1 is released; this is consistent with the assumption that T1 and T2 preferentially bind to L1. However, the fluorescence increases quickly when the concentrations of both targets T1 and T2 exceed that of the threshold L1.

Different cooperative hybridization elements can be cascaded with one another to exhibit more advanced logical functions. Here, the AND gate of FIG. 1 is cascaded to the NOT gate of FIG. 3 to form a reaction network exhibiting NAND logic (FIG. 5C). Ordinarily, this would require one or more strand. However, in this case T3 was designed to be identical in sequence to P1, so that this stage can be eliminated. FIGS. 5D & E show that the NAND network functions as designed: D1, L1, D2, and T4 were present in solution initially, and the observed fluorescence decreases only when both [T1] and [T2] exceed the threshold [L1]. In particular, in this case T1 and T2 were added at time t≈0. No new parameters were fit to the data shown in this figure; rate constants simulated were fitted in previous figures. FIG. 5E provides a 3D summary of the experimental results in FIG. 5D.

EXAMPLE 5

Robustness

Thus far, all reactions have been tested in isolated solutions, in which no nucleic acids other than those needed were present. In order for the designed systems to function in either a biological setting or a complex synthetic chemical network, however, all designed reactions must be robust to a background of nucleic acids that interact nonspecifically.

Here, the robustness of cascaded cooperative hybridization reaction networks is tested by running the NAND reaction network in a solution of poly-N strands (FIG. 6). Various amounts oligonucleotides were added to the NAND reaction network. The poly-N strands are each 50 nt long, with a random (G, C, A, T) base at every position with roughly equal probability. As $4^{50} > 10^{23}$, it is likely that every strand in the poly-N mix is different in sequence. In this experiment, D1, L1, D2, and T4 were present in solution initially; T1, T2, and poly-N were added at time t≈0.

The reaction network functions qualitatively similarly, even in the presence of a 16× excess of poly-N over T1 and T2, attesting to the robustness and specificity of the cooperative hybridization mechanism. A standard hybridization assay is likely to be more disrupted by the presence of these poly-N strands, due to nonspecific binding interactions. Thus, the cooperative hybridization mechanism provides an additional degree of robustness and specificity over typical nucleic acid hybridization.

Other than fluorophore/quencher-labeled oligonucleotides, the DNA strands used did not undergo post-synthesis HPLC or PAGE purification. This was to demonstrate the error robustness of the cooperative hybridization mechanism, which functions despite some fraction of oligonucleotides containing deletions and 5' truncations. Here, denaturing PAGE is used to estimate the purity levels of the oligonucleotides.

FIG. 7A shows the denaturing PAGE that was used to analyze purities, while FIGS. 7B through 7F show the intensity analysis of each lane. Strands T1, T2, P1, and L1 were not post-synthesis purified, while F1 possess the ROX fluorophore and was purified by HPLC. In combination with the results shown in FIG. 6 (discussed above), these results attest to the robustness of the cooperative hybridization mechanism.

EXAMPLE 6

Extensions of Cooperative Hybridization

Cooperative hybridization is a general design principle for engineering nucleic acid devices and is by no means limited to those examples detailed in this manuscript. In this section, two extensions of the cooperative hybridization mechanism are proposed.

Cooperativity is a key feature of ensuring specific binding in both biological enzyme function and synthetic biotechnological devices. To construct devices that sense the simultaneous presence/colocalization of many oligonucleotides, increased cooperativity with Hill coefficient higher than 2 is desirable. One potential method of extending the cooperative hybridization mechanism introduced here is shown in FIG. 8A, wherein three oligonucleotides are hybridized using the system. All three target oligonucleotides must be present to drive the hybridization reactions forward; any two of the three targets in isolation is insufficient and leads to only transient binding. Similar methodology can be used to construct systems requiring four or more cooperative hybridization events. Alternatively, asymmetric branched DNA can also be used to implement three and four-target cooperative hybridization. In cooperative hybridization of three or more oligonucleotides of independent sequence, geometry needs to be considered in addition to hybridization thermodynamics.

The controlled joining of DNA complexes or nanostructures could allow hierarchical, isothermal assembly of larger DNA nanostructures while preserving nanometer addressability. The use of linker oligonucleotides in a sandwich assay-like process, in which each subunit hybridizes irreversibly to the linker, can cause the subunits to be capped by the linker and preclude proper joining (FIG. 8B, top). In the cooperative hybridization mechanism, each subunit individually cannot stably hybridize to the linker, so this problem is averted, as shown in FIG. 8B, bottom. Using this method, it is possible to link many multiple such complexes or nanostructures together in larger more complex structures, as shown schematically in FIG. 8C.

SUMMARY

In the inventive method, a two-stranded complex has been designed so that multiple oligonucleotides of independent sequence can cooperatively and simultaneously hybridize to it. The cooperative hybridization mechanism is robust and modular, smoothly integrating with other dynamic DNA components to form cascaded reaction networks that perform a variety of functions.

The exemplary reactions provided herein were rationally designed on the basis of the biophysics of nucleic acid hybridization, branch migration, and dissociation. Previous characterization of similar reactions has demonstrated that they function robustly across a wide range of solution salinities and temperatures, as well as in the presence of total RNA and cell lysate. (See, e.g., Zhang, D. Y., et al., *Science* 2007, 318, 1121-1125, the disclosure of which is incorporated herein by reference.) Furthermore, similar strand displacement-based RNA devices have been made to assay and regulate gene expression in cells. (See, e.g., Seferos, D. S., et al., *J. Am. Chem. Soc.* 2007, 129, 15477-15479; Isaacs, F. J., et al., *J. Nat. Biotechnol.* 2004, 22, 841-847; and Venkataraman, S., et al., *Proc. Natl. Acad. Sci. U.S.A.* 2010, 107, 16777-16783., the disclosures of each of which are incorporated herein by reference.) Thus, it is likely that many of these devices can be made to function in situ and in vivo for assaying and regulating gene expression.

Moreover, cooperative hybridization was demonstrated to implement analog subtraction and minimum functions. Both can serve important roles in the analysis and evaluation of biological nucleic acids, in which over- and under-expression of an RNA relative to a standard expression level can be indicative of disease. Integrating these elements with amplification and readout also allows for the construction of nucleic acid devices that perform embedded computation within cells, such as determining cell state from microRNA concentrations. These analog primitives can also serve useful functions in the construction of synthetic circuits for controlling nanoscale self-assembly. In biology, cellular differentiation and development are often guided by the local relative expressions of different genes. Similarly, reaction-diffusion systems combining nucleic acid concentration gradients with concentration comparison circuits could lead to the formation of complex patterns and structures.

By combining cooperative hybridization with thresholding mechanisms, digital logic gates and circuits were constructed. Compared to previous implementations of nucleic acid logic gates and circuits based on strand displacement (e.g., Seelig, G., et al., *Science* 2006, 314, 1585-1588, the disclosure of which is incorporated herein by reference), the major advantage of logic gates based on cooperative hybridization is the ease of sample preparation: the two-stranded complexes used for cooperative hybridization did not require any purification, either at the strand level or at the complex level. Furthermore, these systems are robust to nonspecific oligonucleotides coexisting in solution. These technical advantages reduce the labor needed to set up these circuits, thereby facilitating the construction of more complex reaction networks.

The cooperative hybridization mechanism enables more than just nucleic acid detection, quantitation, and logic; it is a fundamentally new design primitive that can allow simultaneity detection, precise timing control, nonlinear signal responses, and nanostructure joining. Integration of the cooperative hybridization mechanism with functional nucleic acids such as aptamers and ribozymes, expanded nucleic acid alphabets, DNA directed chemical synthesis, or other nanomaterials can broaden the set of chemistries that can serve as both input and output of an engineered nucleic acid system. (See, e.g., Bunka, D. H. J. & Stockley, P. G., *Nat. Rev. Microbiol.* 2006, 4, 588-596; Joyce, G. F., *Annu. Rev. Biochem.* 2004, 73, 791-836; Krueger, A. T. & Kool, E. T., *Chem. Biol.* 2009, 16, 242-248; Gartner, Z. J., et al., *Science* 2004, 305, 1601-1605; and Rosi, N. L. & Mirkin, C. A., *Chem. Rev.* 2005, 105, 1547, the disclosures of each of which are incorporated herein by reference.)

The complexity of natural biochemical circuits enables wondrous behaviors of life such as development, metabolism, and reproduction. It remains an outstanding goal of synthetic biology to rationally design reaction networks that exhibit similar spatial/temporal control of biochemistry; the design, demonstration, and integration of modular nucleic acid systems is one promising approach. The inventive cooperative hybridization mechanism demonstrated herein will allow for the construction of novel complex synthetic nucleic acid reaction and control networks.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A cooperative hybridization system comprising:
first and second target oligonucleotide strands, said first and second target oligonucleotide strands being either identical or independent sequences;
a nucleic acid intermediary complex comprising a substrate strand and a protector strand, a binding region of the protector strand being bound to said substrate strand, the substrate strand having a plurality of independent binding domain regions that are complementary to the first and second target oligonucleotide strands for binding to said first and second target oligonucleotide strands, each of the independent binding domain regions being formed from a plurality of individual domains, and said independent binding domain regions being adjacent each other such that, when said nucleic acid intermediary complex hybridizes to said first and second target oligonucleotide strands, said first and second target oligonucleotide strands are co-localized on said substrate strand, wherein the length of the binding region of the protector strand is less than the sum of the lengths of the binding regions of the first and second target oligonucleotide strands, and wherein the binding regions of the first and second target oligonucleotide strands are fully complementary with the independent binding domain regions of the substrate strand, and wherein
the hybridization of one of the first and second target oligonucleotide strands to the substrate strand of said nucleic acid intermediary complex only partially and reversibly displaces the protector strand from said substrate strand; and
wherein the hybridization of both first and second target oligonucleotide strands to the substrate strand irreversibly releases said protector strand from said substrate strand, and produces a dual-hybridized product including both first and second target oligonucleotide strands and substrate strand.

2. The system of claim 1, wherein, during a process of cooperative hybridization of the first and second target oligonucleotide strands to the nucleic acid intermediary complex, an equilibrium exists between a first group consisting of the first and second target oligonucleotide strands and the DNA intermediary complex, and a second group consisting of the dual-hybridized product and the protector strand.

3. The system of claim 2, wherein, when the concentrations of the first and second target oligonucleotide strands are low, the equilibrium favors the first group consisting of the first and second target oligonucleotide strands and the nucleic acid intermediary complex, and when the concentrations of the first and second target oligonucleotide strands are high, the equilibrium favors the second group consisting of the dual-hybridized product and the protector strand.

4. The system of claim 1, wherein the hybridization of one of the first and second target oligonucleotide strands to the substrate strand of the nucleic acid intermediary complex is thermodynamically unfavorable.

5. The system of claim 1, wherein the individual hybridization energy of only one of the first and second target oligonucleotide strands is insufficient to overcome the entropic loss of localizing one of the first and second target oligonucleotide strand on the substrate strand of the nucleic acid intermediary complex; and wherein the collective hybridization energies of both of the first and second target oligonucleotide strands are sufficient to overcome a configuration entropy loss associated with co-localizing the first and second target oligonucleotide strands on the substrate strand of the nucleic acid intermediary complex.

6. The system of claim 1, wherein the length of the protector strand is sufficiently long to prevent spontaneous dissociation the protector strand from said substrate strand.

7. The system of claim 1, wherein the length of one of the independent binding domain regions of the substrate strand is between 2 and 20 nucleotides.

8. The system of claim 1, wherein the first and second target oligonucleotide strands further include at least one dangle or overhang disposed on their one end.

9. The system of claim 1, wherein at least one of the protector strand and the first target oligonucleotide or the second target oligonucleotide of the dual-hybridized product includes a reporter ligand that can be detected by an analytic technique.

10. The system of claim 9, wherein the reporter ligand is a fluorescent reporter selected from one of an organic fluorophore and a quantum dot.

11. The system of claim 1, further comprising at least one catalyst system.

12. The system of claim 1, wherein either the release of the protector strand from the nucleic acid intermediary complex or the production of the dual-hybridized product and the concentration of at least one of the first and second target oligonucleotide strands have a sigmoidal relationship.

13. The system of claim 12, further including a multi-stranded complex reactive to at least one of said first and second target oligonucleotide strands, wherein said multi-stranded complex only reacts with said at least one of said first and second target oligonucleotide strands when the concentration of said at least one of said first and second target oligonucleotide strands is above a specified concentration threshold.

14. The system of claim 12, further including a multi-stranded precursor complex formed from the substrate strand and the first target oligonucleotide strand, said multi-stranded precursor complex being reactive with the protector strand to produce the first target oligonucleotide strand and the nucleic acid intermediary complex, and wherein, based on adding the second target oligonucleotide strand into a solution comprising the multi-stranded precursor complex and the nucleic acid intermediary complex, the second target oligonucleotide strand reacts with the precursor complex before reacting with the nucleic acid intermediary complex.

15. The system of claim 1, further comprising a plurality of catalyst systems in which the release of a product from an initial catalyst system of the catalyst systems acts as a catalyst for a subsequent catalyst system of the catalyst systems.

16. The system of claim 15, wherein the plurality of catalyst systems includes at least a first catalyst system and a second catalyst system, and wherein the catalyst molecule of the first catalyst system and the catalyst molecule of the second catalytic system are binding site independent.

17. The system of claim 1, further comprising a plurality of logic gates.

18. The system of claim 17, wherein the logic gates are selected from the group consisting of AND, OR and NOT.

19. The system of claim 17, wherein the output molecule of the logic gates serves as a catalytic input for at least one catalytic network comprising one or more catalyst systems.

20. The system of claim 19, wherein the plurality of logic gates comprise at least a first catalytic logic gate and a second catalytic logic gate, and wherein the first catalytic logic gate is an AND gate and the second catalytic logic gate is a NOT gate such that the first and second logic gates combine to form a NAND logic gate.

21. The system of claim 1, wherein at least one of the first and second target oligonucleotide strands include one or more DNA nanostructures; and
   wherein the nucleic acid intermediary complex is a freely diffusing linker molecule to link said DNA nanostructures.

22. The system of claim 1, wherein the first and second target oligonucleotide strands are identical in sequence.

23. A cooperative hybridization system comprising:
   at least three target oligonucleotide strands, said target oligonucleotide strands being either identical or independent sequences;
   a nucleic acid intermediary complex comprising a substrate molecule and a protector molecule, a binding region of the protector molecule being bound to said substrate molecule, the substrate molecule having a plurality of independent binding domain regions that are complementary to the target oligonucleotide strands for binding to each of said target oligonucleotide strands, each of the independent binding domain regions being formed from a plurality of individual domains, and said independent binding domain regions being joined together such that, when said at least three target oligonucleotide strands hybridize to said nucleic acid intermediary complex, at least first and second target oligonucleotide strands of said at least three target oligonucleotide strands are co-localized on said substrate molecule, wherein the length of the binding region of the protector molecule is less than the sum of the lengths of the binding regions of the first and second target oligonucleotide strands, and wherein the binding regions of the first and second target oligonucleotide strands are fully complementary with the independent binding domain regions of the substrate molecule, and wherein:
   the hybridization of less than all of the target oligonucleotide strands to the substrate molecule of said nucleic acid intermediary complex only partially and reversibly displaces the protector molecule from the substrate molecule; and
   wherein the hybridization of all of the target oligonucleotide strands to the substrate molecule irreversibly releases said protector molecule from said substrate molecule, and produces a dual-hybridized product including all of the target oligonucleotide strands and the substrate molecule.

24. The system of claim 23, wherein at least one of the protector molecule and the substrate molecule is either a multi-stranded complex or a branched nucleic acid oligonucleotide.

25. The system of claim 23, wherein the independent binding domain regions are joined together via either covalent chemistry or multi-armed double-stranded nucleic acid junctions.

26. The system of claim 25, wherein the independent binding domain regions are selected from the group consisting of custom branched oligonucleotides and non-specifically cross-linked DNA oligonucleotides.

27. The system of claim 25, wherein the covalent chemistry uses a chemical material selected from the group consisting of formaldehyde, cisplatin, psoralens, and nitrous acid.

28. The system of claim 23, wherein at least two of the at least three target oligonucleotide strands are identical in sequence.

29. A method of cooperatively hybridizing at least two target oligonucleotide strands with a nucleic acid intermediary complex, comprising:
   providing at least two target oligonucleotide strands, said at least two target oligonucleotide strands being either identical or independent sequences;
   providing a nucleic acid intermediary complex comprising a substrate strand and a protector strand, a binding region of the protector strand being bound to said substrate strand, the substrate strand having a plurality of independent binding domain regions that are complementary to the at least two target oligonucleotide strands for binding to said at least two target oligonucleotide strands, the independent binding domain regions being joined together such that when the at least two target oligonucleotide strands hybridize to said nucleic acid intermediary complex, the at least two target oligonucleotide strands are co-localized on the substrate strand, wherein the length of the binding region of the protector strand is less than the sum of the lengths of the binding regions of the at least two target oligonucleotide strands, and wherein the binding regions of the at least two target oligonucleotide strands are fully complementary with the independent binding domain regions of the substrate strand; and
   hybridizing the at least two target oligonucleotide strands to said nucleic acid intermediary complex such that the hybridization of less than all of the at least two target oligonucleotide strands to the substrate strand of said nucleic acid intermediary complex partially and reversibly displaces the protector strand from the substrate strand
   while the hybridization of all of the at least two target oligonucleotide strands to the substrate strand irreversibly releases said protector strand from said substrate strand, and produces a dual-hybridized product including the at least two target oligonucleotide strands and substrate strand.

30. The method of claim 29, wherein_, during a process of hybridizing the least two target oligonucleotide strands to said nucleic acid intermediary complex, an equilibrium exists between a first group consisting of the at least two target oligonucleotide strands and the nucleic acid intermediary complex, and a second group consisting of the dual-hybridized product and the protector strand.

31. The method of claim 30, wherein, when the concentrations of the at least two target oligonucleotide strands are low, the equilibrium favors the first group consisting of the at least two target oligonucleotide strands and the nucleic acid intermediary complex, and when the concentrations of the at least two target oligonucleotide strands are high, the equilibrium favors the second group consisting of the dual-hybridized product and the protector strand.

32. The method of claim 29, further comprising monitoring the release of at least one molecule selected from the group consisting of the at least two target oligonucleotide strands, said dual-hybridized product and said protector strand to provide real-time detection and quantitation of the concentration of said at least one molecule.

33. The method of claim 29, wherein the hybridization of less than all of the target oligonucleotide strands to the substrate strand of said nucleic acid intermediary complex is thermodynamically unfavorable.

34. The method of claim 29, wherein the at least two oligonucleotide strands comprise at least a first target oligonucleotide strand and a second target oligonucleotide strand, and, when a known concentration of the first target oligonucleotide strand and an excess concentration of the nucleic acid intermediary complex are provided, the stoichiometric consumption of the second target oligonucleotide strand are monitored to determine the concentration of the second target oligonucleotide strand.

35. The method of claim 29, wherein the individual hybridization energies of less than all of the at least two target oligonucleotide strands are insufficient to overcome the entropic loss of localizing less than all of target oligonucleotide strands on the substrate strand of the nucleic acid intermediary complex.

36. The method of claim 29, wherein the collective hybridization energies of all of the at least two target oligonucleotide strands are sufficient to overcome a configuration entropy loss associated with co-localizing all of the target oligonucleotide strands on the substrate strand of the nucleic acid intermediary complex.

37. The method of claim 29, wherein at least one of the target oligonucleotide strands, the protector strand and the target oligonucleotide strands of the dual-hybridized product includes a reporter ligand that can be detected by an analytic technique.

38. The method of claim 29, wherein either the release of the protector strand from the nucleic acid intermediary complex or the production of the dual-hybridized product and the concentration of at least one of the at least two target oligonucleotide strands have a sigmoidal relationship.

39. The system of claim 29, wherein the at least two target oligonucleotide strands include at least a first and second target oligonucleotide strands.

40. The method of claim 29, wherein the least two target oligonucleotide strands comprises at least three target oligonucleotide strands, and wherein at least one of the protector and the substrate strand is either a multi-stranded complex or a branched nucleic acid oligonucleotide such that three or more target oligonucleotide strands of the at least three target oligonucleotide strands can hybridize to the substrate strand.

41. The method of claim 29, wherein at least one of the at least two target oligonucleotide strands are either covalently or non-covalently bound to a DNA nanostructure molecule; and wherein the nucleic acid intermediary complex is a freely diffusing linker molecule to link said DNA nanostructure molecule.

* * * * *